(12) United States Patent
Tong

(10) Patent No.: US 11,331,302 B2
(45) Date of Patent: May 17, 2022

(54) TRANSMUCOSAL DELIVERY OF TOCOTRIENOL

(71) Applicant: INVICTUS BIOTECHNOLOGY PTY LTD., Melbourne (AU)

(72) Inventor: Glenn Tong, Hawthorn (AU)

(73) Assignee: INVICTUS BIOTECHNOLOGY PTY LTD., Melbourne (AU)

( * ) Notice: Subject to any disclaimer, the term of this patent is extended or adjusted under 35 U.S.C. 154(b) by 0 days.

(21) Appl. No.: 15/929,297

(22) Filed: Apr. 23, 2020

(65) Prior Publication Data

US 2020/0246306 A1 Aug. 6, 2020

Related U.S. Application Data

(62) Division of application No. 14/435,607, filed as application No. PCT/AU2013/001310 on Nov. 13, 2013, now Pat. No. 10,675,265.

(30) Foreign Application Priority Data

Nov. 13, 2012 (AU) ................................ 2012904937
Dec. 11, 2012 (AU) ................................ 2012905406

(51) Int. Cl.
*A61K 31/355* (2006.01)
*A61K 9/00* (2006.01)
*A61K 31/353* (2006.01)

(52) U.S. Cl.
CPC ............ *A61K 31/355* (2013.01); *A61K 9/006* (2013.01); *A61K 31/353* (2013.01)

(58) Field of Classification Search
CPC ...... A61K 31/335; A61K 9/00; A61K 31/353; A61P 3/06; A61P 3/10; A61P 9/10; A61P 9/12; A61P 17/14; A61P 17/16
See application file for complete search history.

(56) References Cited

U.S. PATENT DOCUMENTS 8,951,566 B2 2/2015 Ko
2002/0061924 A1 5/2002 Terao et al.
(Continued)

FOREIGN PATENT DOCUMENTS

AU 2010262738 10/2011
CN 1775289 A 5/2006
(Continued)

OTHER PUBLICATIONS

Regenstein et al., Woodland Publishing Series in Food Science By-Products Collagen and Gel from Marines,, 2007.*
(Continued)

*Primary Examiner* — Carlos A Azpuru
(74) *Attorney, Agent, or Firm* — Nixon & Vanderhye

(57) ABSTRACT

The present invention relates to pharmaceutical compositions formulated for transmucosal delivery, and in particular sublingual delivery, comprising at least one tocotrienol or derivative thereof together with one or more pharmaceutically acceptable excipients. The present further relates to the use of said compositions for treating or preventing post exercise muscle soreness, delayed onset muscle soreness, cardiac fibrosis, hypertension, inflammation, stroke, cancer, elevated cholesterol and/or triglycerides, baldness, hypertrophy, conditions resulting from radiation exposure, stabilizing and/or controlling blood glucose levels, and improving exercise endurance and capacity.

11 Claims, 10 Drawing Sheets

(56) References Cited

U.S. PATENT DOCUMENTS

| | | |
|---|---|---|
| 2005/0209315 A1 | 9/2005 | Papas et al. |
| 2009/0258865 A1 | 10/2009 | Cartt et al. |
| 2011/0172312 A1 | 7/2011 | Miller et al. |
| 2012/0058962 A1 | 3/2012 | Cumming et al. |
| 2012/0122969 A1 | 5/2012 | Miller |
| 2012/0219624 A1 | 8/2012 | Ko |
| 2012/0295985 A1 | 11/2012 | Miller et al. |
| 2013/0065886 A1 | 3/2013 | Cartt et al. |
| 2013/0116336 A1 | 5/2013 | Shrader |

FOREIGN PATENT DOCUMENTS

| | | |
|---|---|---|
| EP | 1 199 076 | 4/2002 |
| EP | 1 230 923 | 8/2002 |
| EP | 1 270 004 | 1/2003 |
| JP | H08-92050 A | 4/1996 |
| JP | 11-49767 | 2/1999 |
| JP | 2001-342133 | 12/2001 |
| JP | 2002-037727 A | 2/2002 |
| JP | 2002-114678 | 4/2002 |
| JP | 2002-308768 | 10/2002 |
| JP | 2003-512402 A | 4/2003 |
| JP | 2007-524594 | 8/2007 |
| JP | 2012-531411 | 12/2012 |
| WO | WO 2004/086412 | 10/2004 |
| WO | WO 2005/009135 | 2/2005 |
| WO | WO 2009/126866 | 10/2009 |
| WO | WO 2010/144943 | 12/2010 |
| WO | WO 2010/151348 | 12/2010 |
| WO | WO 2011/082355 | 7/2011 |
| WO | WO 2011/126998 | 10/2011 |
| WO | WO 2012/068552 | 5/2012 |
| WO | WO 2012/109694 | 8/2012 |
| WO | WO 2012/174158 | 12/2012 |

OTHER PUBLICATIONS

Abuasal et al., "Enhancement of Intestinal Permeability Utilizing Solid Lipid Nanoparticles Increases γ-Tocotrienol Oral Bioavailability" *Lipids*, 47: 461-469 (2012).

Abuasal et al., "Comparison of the intestinal absorption and bioavailability of γ-tocotrienol and -60 -tocopherol; in vitro, in situ and in vivo studies" *Biopharmaceutics & Drug Disposition*, 33: 246-256 (2012).

Akira Yamamoto, "Improvement of Gastrointestinal and Transmucosal Absorption of Poorly Absorbable Drugs and Development of Novel Dosage Forms of These Drugs" Apr. 2012, pp. 208-219.

Nibha et al., "An Overview on: Sublingual Route for Systemic Drug Delivery"—International Journal of Research in Pharmaceutical and Biomedical Sciences, vol. 3 (2) Apr.-Jun. 2012.

Ashraf et al.,"Considerations in Developing Sublingual Tablets—An Overview" *Pharmaceutical Technology Europe*, 38(11): 33-40 (Nov. 2014).

Black et al. "Palm tocotrienols protect ApoE +/-mice from diet-induced atheroma formation" J Nutrition 2000;130(10):2420-6 (2000).

Bloomer et al., "Prior exercise and antioxidant supplementation: effect on oxidative stress and muscle injury" *Journal of the International Society of Sports Nutrition*, 2007,4:9, pp. 1-10, http://www.jissn.eom/content/4/1/9.

Cheung et al. "Delayed Onset Muscle Soreness: Treatment Strategies and Performance Factors" *Sports Med*, 2003; 33(2): 145-164.

Cleak et al., "Delayed onset muscle soreness: Mechanisms and management" *Journal of Sports Sciences*, 10:4, 325-341, (1992), DOI: 10.1080/02640419208729932.

Close et al., "Eccentric exercise, isokinetic muscle torque and delayed onset muscle; soreness: the role of reactive oxygen species"; Eur. J. Appl. Physiol, vol. 91, p. 615-621 (2004).

Dawson et al., "Effect of Vitamin C and E Supplementation on Biochemical and Ultrastructural Indices of Muscle Damage after a 21 km Run", Int. J. Sports Med.; vol. 23, p. 10-15 (2002).

Fairus et al., "Alpha-tocotrienol is the most abundant tocotrienol isomer circulated in plasma and lipoproteins after postprandial tocotrienol-rich vitamin E supplementation" Nuttition Journal 2012 11:5.

Fang et al. "Vitamin E tocotrienols improve insulin sensitivity through activating peroxisome proliferator-activated receptors" Mol Nutr Food Res, 53: 1-8 (2009).

Fernandes Cruzat et al. "Current Aspects about Oxidative Stress, Physical exercise and supplementation", Rev Bras Med Esprte-vol. 13, No. 5, 2007 p. 304e-310e§.

Fu et al., "Novel tocotrienol-entrapping vesicles can eradicate solid tumors after intravenous administration" J Control Release Aug. 25, 2011; 154(1 ):20-26.

Fu et al., "Bioavailability of tocotrienols: evidence in human studies", Nutrition & Metabolism; vol. 11, No. 5, p. 1-10 (2014).

Gangwar, M. et al. "Recent advances in various emerging vesicular systems: An overview", Asian Pacific Journal of Tropical Biomedicine (2012) S1176-S1188.

Gee, P.T., "Unleashing the untold and misunderstood observations on vitamin E" Genes & Nutrition, Feb. 2011, vol. 6, Issue 1, p. 5-16.

Ghosh et al. "Gamma-tocotrienol, a tocol antioxidant as a potent radioprotector" Int J Radiat Biol 85(7):598-606 (2009).

Gleeson et al., "Effect of exercise-induced muscle damage on the blood lactate response to incremental exercise in humans" *Eur J Appl Physiol*, 77: 292-295 (1998).

Gupta, S. et al. "Polyether based amphiphiles for delivery of active components", Polymer 53 (2012) 3053-3078.

Hay YK, et al. <http://www.tocotrienol.ora/bioavailability-study.html> (accessed Jun. 23, 2016).

Hood, E. et al. "Nanocarriers for vascular delivery of antioxidants", Nanomedicine (Lond). Sep. 2011; 6(7): 1257-1272.

Hosomi et al., "Affinity for α-tocopherol transfer protein as a determinant of the biological activities of vitamin E analogs" *FEBS Letters*, 409: 105-108 (1997).

Hussein et al. "d-δ-tocotrienol-mediated suppression of the proliferation of human PANC-1, MIA PaCa-2, and BxPC-3 pancreatic carcinoma cells" Pancreas 38(4):e124-36.

Ikeda et al. "Dietary α-tocopherol decreases a tocotrienol but not δ-tocotrienol concentration in rats" J Nutr Feb. 2003;133(2):428-34.

Ikeda S, et al., "Complexation of tocotrienol with γ-cyclodextrin enhances intestinal absorption of tocotrienols in rats" Bioscience, Biotechnology and Biochemistry 74, 1452-1457, 2010.

Intention to Grant issued in EP Appln. No. 13 854 440,8 dated Oct. 8, 2018.

International Search Report for PCT/AU2013/001310, ISA/AU, dated Feb. 5, 2014.

Japanese Office Action issued in Appln. No. 2015-540965 dated Sep. 5, 2017 (w/ translation).

Keong et al., "Effects of palm vitamin E supplementation on exercise-induced oxidative stress and endurance performance in the heat". Journal of Sports Science and Medicine 5, 629-639 (2006).

Khanna et al. "Molecular basis of vitamin E action: tocotrienol modulates 12-lipoxygenase, a key mediator of glutamate induced neurodegeneration" J Biol Chem 2003; 278:43508-43515.

Khor et al. "Lipidaemic effects of tocotrienols, tocopherols and squalene: studies in the hamster" Asia Pacific J Clin Nutr (1997) 6(1):36-40.

Khosla et al. "Postprandial levels of the natural vitamin E tocotrienol in human circulation" Antioxidants & Redox Signaling 8(5-6): 1059-68 (2006).

Kuhad et al. "Suppression of NF-κβ signaling pathway by tocotrienol can prevent diabetes associated cognitive deficits" Pharmacology, Biochemistry and Behavior 92(2):251-259 (2009).

Kyparos et al., "Effect of 5-day vitamin E supplementation on muscle injury after downhill running in rats", Eur. J. Appl. Physiol, vol. 111, p. 2257-2569 (2011).

Beoy et al., "Effects of Tocotrienol Supplementation on Hair Growth in Human Volunteers", Tropical Life Sciences Research, vol. 21 (2), p. 91-99 (2010).

Lee et al.,"Effects of tocotrienol-rich fraction on exercise endurance capacity and oxidative stress in forced swimming rats", Eur. J. Appl. Physiol, V. 107, p. 587-595 (2009).

(56) References Cited

OTHER PUBLICATIONS

M. J. Rathbone et al., "Chapter 2, Overview of Oral Mucosal Delivery", Oral Mucosal Drug Delivery and Therapy, XVI, p. 17-26 (2015).
Madhav et al., "Orotransmucosal drug delivery systems: A review", Journal of Controlled Release, vol. 140, p. 2-11 (2009).
Mannila et al., "Precipitation complexation method produces cannabidiol/β cyclodextrin inclusion complex suitable for sublingual administration on cannabidiol" Journal of Pharmaceutical Sciences 96, 312-319, 2007.
Mathai et al., 2011, (see Torres et al. "Enzymatic Modification for Ascorbic Acid and α-Tocopherol Enhances their Stability in Food and Nutritional Applications" The Open Food Science Journal 2008, 2, 1-9).
McGinley et al., "Does Antioxidant Vitamin Supplemental Protect against Muscle Damage?", Sports Med. vol. 39, No. 12, p. 1011-1032 (2009).
McLeay et al., "Effect of New Zealand blueberry consumption on recovery from eccentric exercise-induced muscle damage" *Journal of the International Society of Sports Nutrition* 2012, 9:19, 12 pages.
Nakamura et al., "Oral Toxicity of a tocotrienol preparation in rats" Food Chem Toxicol Aug. 2001; 39(8): 799-805.
Nesaretnam et al. "Tocotrienols: inflammation and cancer" Ann N Y Acad Sci. Jul. 2011;1229:18-22.
Nikanjam et al, "Synthetic nano-low density lipoprotein as targeted drug delivery vehicle for glioblastoma multiforme," International Journal of Pharmaceutics (2006) pp. 1-9.
O'Byrne et al., "Studies of LDL Oxidation Following α-, γ-, or δ-tocotrienyl acetate supplementation of hypercholesterolemichumans"*Free Radical Biology & Medicine*, 29(9):834-845 (2000).
Paliwal, R et al. "Effect of lipid core material on characteristics of solid lipid nanoparticles designed for oral lymphatic delivery", Nanomedicine: Nanotechnology, Biology and Medicine 5 (2009) 184-191.
Patel et al., "Oral tocotrienols are transported to human tissues and delay the progression of the model for end-stage liver disease score inpatients" Journal of Nutrition 2012, 142 (3): 512-519.
Qureshi et al. "Dietary α-tocopherol attenuates the impact of γ-tocotrienol on hepatic 3-hydroxy-3-methylglutaryl coenzyme A reductase activity in chickens" J Nutrition Feb. 1996; 126(2):389-94.
Reboul et al., "Proteins involved in uptake, intracellular transport and basolateral secretion of fat-soluble vitamins and carotenoids by mammalian enterocytes" *Progress in Lipid Research*, 50: 388-402 (2011).
Sagnella, S.M. et al. "Anandamide and analogous endocannabinoids: a lipid self-assembly study", Soft Matter, 2011, 7, 5319-5328.
Sen et al., "Tocotrienols in health and disease: The other half of die natural vitamin E family", Molecular Aspects of Medicine, vol. 28, p. 692-728 (2007).
Serbinova et al. "Free radical recycling and intramembrane mobility in the antioxidant properties of α-tocopherol and α-tocotrienol", Free Radical Biology & Medicine 10(5):263-75 (1991).
Shibata et al. "α-Tocopherol attenuates the cytotoxic effect of δ-tocotrienol in human colorectal adenocarcinoma cells" Biocehm. Piophys. Res. Commun. 397(2):214-219 (2010).
Song et al. "Insig-dependent Ubiquitination and Degradation of 3-Hydroxy-3-methylglutaryl Coenzyme A Reductase Stimulated by δ- and γ-Tocotrienols" The Journal of Biological Chemistry 281 (35):25054-61 (2006).
Sontag et al. "Influence of major structural features of tocopherols and tocotrienols on their ω-oxidation by tocopherol-ω-hydroxylase" J. Lipid Res. 48(5): 1090-1098 (2007).
Stampfer et al., "Epidemiologic evidence for vitamin E in prevention of cardiovascular disease", Am. J. Clin, Nutr., 62(suppl):1665S-9S (1995).
The Handbook of Pharmaceutical Excipients, Rowe, Raymond C; Sheskey, Paul J; Cook, Walter G; Fenton, Marian E (eds), Pharmaceutical Press.
Vraka et al "Synthesis and study of the cancer cell growth inhibitory properties of α-, γ-tocopheryl and γ-tocotrienyl 2-phenylselenyl succinates" Bioorganic & Medicinal Chemistry 14 (2006) 2684-2696.
Wan et al., "Muscle fatigue: general understanding and treatment" *Experimental & Molecular Medicine* (2017) 49, e384, 11 pages; doi:10.1038/emm.2017.194.
Yap et al. "Pharmacokinetics and bioavailability of α-,γ- and δ-tocotrienols under different food status" J Pharm Pharmacol Jan. 2001; 53(1):67-71.
Office Action issued in Japanese Patent Application No. 2020-171008 dated Dec. 7, 2021 with English translation provided.
Aggarwal, B. et al., "Tocotrienols, the vitamin E of the 21st century: Its potential against cancer and other chronic diseases," Biochemical Pharmacology 80 (2010) 1613-1631.
Reznick, A. et al., "Vitamin E Inhibits Protein Oxidation in Skeletal Muscle of Resting and Exercised Rats," Biochemical and Biophysical Research Communications, vol. 189, No. 2, pp. 801-806, Dec. 15, 1992.
Sen, C. et al., "Tocotrienols: The Emerging Face of Natural Vitamin E," Vitamins and Hormones, vol. 76, 2007.
Wong, R. et al., "Tocotrienol research: past into present," Nutrition Reviews, vol. 70(9):483-490, 2012.

\* cited by examiner

| R¹ | R² | |
|---|---|---|
| CH₃ | CH₃ | α-Tocopherol |
| CH₃ | H | β-Tocopherol |
| H | CH₃ | γ-Tocopherol |
| H | H | δ-Tocopherol |

| R¹ | R² | |
|---|---|---|
| CH₃ | CH₃ | α-Tocotrienol |
| CH₃ | H | β-Tocotrienol |
| H | CH₃ | γ-Tocotrienol |
| H | H | δ-Tocotrienol |

TRANSMUCOSAL DELIVERY OF TOCOTRIENOL

This application is a Divisional of U.S. application Ser. No. 14/435,607 filed Apr. 14, 2015, which is the U.S. national phase of International Application No. PCT/AU2013/001310 filed Nov. 13, 2013, which designated the U.S. and claims the benefit of AU Application No. 2012905406 filed Dec. 11, 2012 and AU Application No. 2012904937 filed Nov. 13, 2012, the entire contents of each of which are hereby incorporated by reference.

FIELD OF THE INVENTION

The present invention relates to pharmaceutical compositions including tocotrienols and derivatives thereof, for transmucosal (such as buccal, sublingual and nasal) administration.

BACKGROUND OF THE INVENTION

An essential nutrient for the body, vitamin E is made up of four tocopherols (alpha, beta, gamma, delta) and four tocotrienols (alpha, beta, gamma, delta), with the difference between tocotrienols and tocopherols lying in the unsaturated side chain having three double bonds in its farnesyl isoprenoid tail for tocotrienols whereas these double bonds are single bonds in the tocopherols (FIG. 1).

Tocotrienols occur in selected vegetable oils such as palm and rice bran, certain types of fruits such as annatto and saw palmetto, nuts such as macadamia and plant products such as rubber tree latex. The tocotrienol component of the total Vitamin E is generally lower than the tocopherol component.

Chemically, each of the tocotrienol and tocopherol isomers have an antioxidant activity due to their ability to donate a hydrogen atom (a proton plus electron) from the hydroxyl group on the chromanol ring to a free radical in the body. This process inactivates ("quenches") the free radical by effectively donating a single unpaired electron (which comes with the hydrogen atom) to the radical.

Vitamin E has long been known for its antioxidative properties against lipid peroxidation in biological membranes and alpha-tocopherol has previously been considered to be the most active form. However, in vivo, tocotrienols are more powerful antioxidants, and lipid oxygen radical absorbance capacity (ORAC) values are highest for delta-tocotrienol. Recent data would suggest that tocotrienols are better antioxidants than tocopherols at preventing cardiovascular diseases and cancer, and in the treatment of diabetes. Current formulations of vitamin E supplements are composed mainly of alpha-tocopherol.

Tocotrienols have many uses beyond their lipid-soluble antioxidant property. They specifically inhibit biosynthesis of cholesterol by the liver through enhanced degradation of the enzyme HMG-CoA reductase (Song et al "Insig dependent ubiquitination and degradation of 3-hydroxy-3-methylglutaryl coenzyme a reductase by delta- and gamma-tocotrienols" The Journal of Biological Chemistry 281 (35): 25054-61). Tocotrienols have been shown to inhibit inflammatory pathways mediated by NF-κB (Nesaretnam et al "Tocotrienols: inflammation and cancer" Ann N Y Acad Sci. 2011 July; 1229:18-22). They have also been identified as agonists to peroxisome proliferator-activated receptor (PPAR), in particular PPAR-gamma, which is an insulin-sensitiser in addition to increasing adipogenesis (Fang et al "Vitamin E tocotrienols improve insulin sensitivity through activating peroxisome proliferator-activated receptors" Mol Nutr Food Res 2010 March; 54(3): 345-52). Indeed, tocotrienols influence many more biochemical pathways than tocopherols, and are being developed as treatments for inflammation, ischaemia-associated diseases such as stroke and myocardial infarct, dyslipidaemia and even cancer (Khosla et al "Postprandial levels of the natural vitamin E tocotrienol in human circulation" Antioxidants & Redox Signalling 8(5-6): 1059-68).

Tocotrienols have been shown to or have the potential to:
have strong anti-oxidant properties (Serbinova et al "Free radical recycling and intramembrane mobility in the antioxidant properties of alpha-tocopherol and alpha-tocotrienol" Free Radical Biology & Medicine 10(5): 263-75).
reverse hypertension and cardiac fibrosis (Black et al "Palm tocotrienols protect ApoE+/−mice from diet induced atheroma formation" J Nutrition 2000; 130 (10):2420-6).
improve control of blood glucose and insulin response (Kuhad et al (2009) "Suppression of NF-κβ signalling pathway by tocotrienol can prevent diabetes associated cognitive defects" Pharmacology Biochemistry, and Behaviour 92(2):251-9)
specifically inhibit biosynthesis of cholesterol by the liver, i.e., they can lower cholesterol levels and ameliorate dyslipidaemia (Song et al "Insig dependent ubiquitination and degradation of 3-hydroxy-3-methylglutaryl coenzyme a reductase by delta- and gamma-tocotrienols" The Journal of Biological Chemistry 281 (35): 25054-61)
inhibit inflammatory pathways mediated by cyclooxygenase-2 and 12-lipoxygenase, i.e., they can be used as treatments for inflammation (Khanna et al "Molecular basis of vitamin E action: tocotrienol modulates 12-lipoxygenase, a key mediator of glutamate induced neurodegeneration" J Biol Chem 2003; 278:43508-43515)
potentially be useful as treatments for stroke, myocardial infarct, and even cancer (Hussein et al "d-Delta-tocotrienol-mediated suppression of the proliferation of human PANC-1, MIA PaCa-2, and BxPC-3 pancreatic carcinoma cells" Pancreas 38(4):e124-36)
improve exercise endurance and improve muscle glycogen levels (Lee et al "Effects of tocotrienol-rich fraction on exercise endurance capacity and oxidative stress in forced swimming rats" Eur J Appl Physiol 2009; 107(5):587-95)
act as radioactive countermeasures for persons exposed to radiation (Ghosh et al "Gamma-tocotrienol, a tocol antioxidant as a potent radioprotector" Int J Radiat Biol 85(7):598-606)

Dietary lipids and fat-soluble vitamins must first be emulsified by bile and packaged into micelles for transport into the circulation to be absorbed from the gastrointestinal tract. Bile excretion is dependent on the level and type of dietary fat consumed, and studies have shown that tocotrienol absorption is reduced in fasted versus full-fed individuals (Yap et al "Pharmacokinetics and biovailability of alpha-, gamma- and delta-tocotrienols under different food status" J Pharm Pharmacol 2001 January; 53(1):67-71). Oral administration of isolated tocotrienols by gavage or gel capsules may therefore lack sufficient fat content to stimulate enough bile excretion into the small intestine that would be necessary to promote tocotrienol absorption.

Following oral administration, tocotrienols are absorbed from the intestine and transported to the systemic circulation through the lymphatic pathway. Studies in humans have shown that gamma-tocotrienol relative bioavailability increased when administered with food and that in the fasted human, plasma tocotrienol concentration do not significantly increase following tocotrienol ingestion (Yap et al "Pharmacokinetics and biovailability of alpha-, gamma- and delta-tocotrienols under different food status" J Pharm Pharmacol 2001 January; 53(1):67-71). Although food enhances gamma-tocotrienol absorption by stimulating excretion of bile and pancreatic enzymes that enhance the formation of mixed micelles, gamma-tocotrienol absorption remains limited and far from complete.

It would appear that it is very difficult to obtain and/or sustain therapeutic levels of gamma-tocotrienol in the blood and target tissues by simple oral administration because absorption and transport mechanisms within the body are extremely limiting and display significant preference for alpha-tocopherol. Although various tocotrienol-containing products are already commercially available, these products are simply capsules filled with a blend of various tocopherols and tocotrienol oils and sold as nutritional supplements for oral consumption. This type of formulation or delivery system displays poor solubility in the fluids of the intestine and high oral doses of tocotrienols inhibit its own absorption from the gut. Consequently, only relatively low levels of tocotrienol will reach the blood when simply formulated as an oil-filled capsule delivery system and hence one strategy that is in current use is to use an emulsifying agent to enhance absorption from the gastrointestinal tract.

Tocotrienols can be associated with the lipoprotein particles termed chylomicrons and taken up via the gut lacteal system where they are transported via the lymphatic system to the circulation. From here, the degree of uptake by tissues varies. Some reports say that the majority ends up in skin and adipose tissue, with lower uptake into other tissues (Gee, P. T., "Unleashing the untold and misunderstood observations on vitamin E" Genes & Nutrition February 2011, Vol 6, Issue 1, p 5-16). They can be incorporated into very low density lipoproteins at least in part mediated by binding to alpha-tocopherol transport protein to be taken up into the liver and repackaged into lipoproteins for export to other tissues via the circulation. For example, gamma-tocotrienol and delta-tocotrienol seem to have very low levels of uptake by key metabolic tissues such as skeletal muscle and liver.

Tocotrienol supplementation did not appear to confer a therapeutic effect in moderate-sized clinical trials in patients with dyslipidaemia, despite the fact that plasma tocotrienols were elevated by the oral supplementation. This may have been due to inadequate dosage, the competitive effects of the alpha-tocopherol that were co-supplemented, or insufficient levels of tocotrienols being present in the liver so as to inhibit biosynthesis of cholesterol). This meant that reports of positive effects were restricted to rodent studies and some small human trials. It has therefore been doubted as to whether the beneficial effects found in animal studies could be translated to humans, and whether absorbtion/storage of tocotrienols was deficient. It is also clear that alpha-tocopherol has the highest affinity for the transport protein (named alpha-tocopherol transport protein-alpha-TTP) and that tocotrienols appear to be more rapidly metabolised than alpha tocopherol, perhaps due to their unsaturated isoprenoid tail and reduced stabilization by alpha-UP due to competition from alpha-tocopherol. It was thought that the lack of any beneficial effect being observed in these studies was either due to the poor bioavailability of orally delivered tocotrienols, or the competitive effects of alpha-tocopherol present in the compositions or a combination of both of these factors.

Given the potential clinical benefits of tocotrienols, and their low toxicity (Nakamura et al, "Oral Toxicity of a tocotrienol preparation in rats" Food Chem Toxicol 2001 August; 39(8): 799-805), it would be useful to provide formulations of tocotrienols with higher bioavailablity than has been possible to date. Attempts have been made to improve the bioavailability of tocotrieniols by incorporating them into lipid nanoparticles or transferrin-bearing multilamellar vesicles, which appears to enhance the antitumour effect of tocotrienols by up to 70-fold (Fu et al, "Novel tocotrienol-entrapping vesicles can eradicate solid tumours after intravenous administration" J Control Release 2011 Aug. 25; 154(1):20-6). However, such formulations are limited in that they must be introduced intravenously (which is not practical or suitable for non-clinical applications and have limited market acceptance for all but the most serious and life-threatening therapeutic indications) and are dependent upon the use of tocopheryl based multilamellar vesicles which may themselves interfere with the activity of the tocotrienols present.

There is a relatively low availability and uptake of tocotrienols into key metabolic tissues such as muscle and liver via oral administration. In a recent paper, supplementation of 400 mg tocotrienols per day for 12 weeks only achieved low or sub-nanomolar/g levels in tissues, and the blood level remained below 2 umol/L in all males. (Patel et al, Oral tocotrienols are transported to human tissues and delay the progression of a model of end-stage liver disease", *Journal of Nutrition* 2012, 142 (3): 512-519). Therefore the need exists for a method of delivering higher levels of tocotrienols into these tissues while minimising metabolic degradation by the liver.

SUMMARY OF THE INVENTION

The inventors of the present invention have found that the administration of tocotrienols by a transmucosal delivery route provides for enhanced bioavailability when compared with orally administered tocotrienols.

Accordingly, the present invention relates a pharmaceutical composition formulated for transmucosal delivery including at least one tocotrienol or derivative thereof together with one or more pharmaceutically acceptable excipients.

In a preferred embodiment, the transmucosal delivery is sublingual or buccal delivery.

In a further preferred embodiment, the composition includes at least one tocotrienol or derivative thereof and at least one tocopherol, wherein the tocopherol component is lower than the tocotrienol component.

In a further preferred embodiment, the composition includes at least one tocotrienol or derivative thereof in the form of a tocotrienol rich fraction of a vitamin E extract, wherein the alpha tocopherol component is lower than the tocotrienol component.

In a further preferred embodiment, the composition includes a tocopherol and the ability of the tocopherol to interfere or compete with the therapeutic activity of the tocotrienol, or derivative thereof has been eliminated, reduced or minimized.

The present invention further relates to a method of treating or preventing a disease or condition amenable to treatment with a tocotrienol including transmucosal administration of at least one tocotrienol or derivative thereof.

In a preferred embodiment, the tocotrienol or derivative thereof is administered sublingually or buccally.

In a further preferred embodiment, the tocotrienol or derivative thereof is administered in a pharmaceutical tablet, film, wafer, gum, powder, spray, solution or gel formulation.

In a further preferred embodiment the disease or condition is selected from the group consisting of: post exercise muscle soreness, delayed onset muscle soreness, cardiac fibrosis, hypertension, inflammation, stroke, cancer, elevated cholesterol and/or triglycerides, baldness, and a condition resulting from radiation exposure.

The present invention further relates to a method of improving exercise endurance including transmucosal administration of at least one tocotrienol or derivative thereof.

The present invention further relates to a method of promoting weight and body fat loss including transmucosal administration of at least one tocotrienol or derivative thereof.

The present invention further relates to a method of stabilizing and/or controlling blood glucose levels in an animal including transmucosal administration of least one tocotrienol, or derivative thereof.

The present invention further relates to a transmucosal pharmaceutical composition including at least one tocotrienol or derivative thereof for use in the prevention or treatment of a disease or condition amenable to treatment with a tocotrienol.

In a preferred embodiment, the transmucosal pharmaceutical composition is formulated for sub-lingual or buccal administration.

In a further preferred embodiment, the transmucosal pharmaceutical composition is in the form of a tablet, film, wafer, gum, powder, spray, solution or gel.

The present invention further relates to a transmucosal pharmaceutical composition comprises a tocotrienol rich vitamin E fraction wherein the alpha tocopherol component is lower than the tocotrienol component.

In a further preferred embodiment, the transmucosal pharmaceutical composition comprising a tocotrienol rich fraction wherein the alpha tocopherol component makes up not more than about 10% of the vitamin E fraction.

In a further preferred embodiment the disease or condition is selected from the group consisting of: post exercise muscle soreness, delayed onset muscle soreness, cardiac fibrosis, hypertension, inflammation, stroke, cancer, elevated cholesterol and/or triglycerides, baldness, and a condition resulting from radiation exposure.

The present invention further relates to a transmucosal pharmaceutical composition including at least one tocotrienol or derivative thereof for use in improving exercise endurance in an animal.

The present invention further relates to a transmucosal pharmaceutical composition including at least one tocotrienol or derivative thereof for use in promoting weight loss in an animal.

The present invention further relates to a transmucosal pharmaceutical composition including at least one tocotrienol or derivative thereof for use in stabilizing and/or controlling blood glucose levels in an animal.

The present invention further relates to the use of at least one tocotrienol or derivative thereof in the preparation of a medicament for transmucosal administration.

The present invention further relates to tocotrienol for use in transmucosal administration.

The present invention further relates to the use of at least one tocotrienol or derivative thereof in the preparation of a medicament for the prevention or treatment of a disease or condition amenable to treatment with a tocotrienol, wherein the medicament is formulated for transmucosal administration.

In a preferred embodiment, the medicament is formulated for sublingual or buccal administration.

In a further preferred embodiment, the medicament is formulated for sublingual administration and is in the form of a tablet, film, wafer, gum, powder, spray, solution or gel.

The present invention further relates to a pharmaceutical composition for treating or preventing a disease or condition amenable to treatment with a tocotrienol, including a therapeutically effective amount of at least one tocotrienol or derivative thereof and one or more excipients suitable for transmucosal drug administration.

In a preferred embodiment, the pharmaceutical composition is formulated for sublingual or buccal administration.

In a further preferred embodiment, the pharmaceutical composition is formulated for sublingual administration and is in the form of a tablet, film, wafer, gum, powder, spray, solution or gel.

The present invention further relates to a method of increasing the bioavailability of a tocotrienol administered to an animal including transmucosal administration of at least one tocotrienol or derivative thereof.

The present invention further relates to a method of minimizing the tocotrienol dosage required to achieve a therapeutic effect in an animal including transmucosal administration of at least one tocotrienol or derivative thereof.

The present invention further relates to a transmucosal pharmaceutical composition including at least one tocotrienol or derivative thereof for use in increasing the bioavailability of a tocotrienol administered to an animal.

The present invention further relates to a transmucosal pharmaceutical composition including at least one tocotrienol or derivative thereof for use in minimizing the dosage required to achieve a therapeutic effect by the administration of a tocotrienol in an animal.

The present invention further relates to the use of a transmucosal pharmaceutical composition including at least one tocotrienol or derivative thereof for the prevention or treatment of a disease or condition amenable to treatment with a tocotrienol.

In a preferred embodiment, the transmucosal pharmaceutical composition is formulated for sub-lingual or buccal administration.

In a further preferred embodiment, the transmucosal pharmaceutical composition is in the form of a tablet, film, wafer, gum, powder, spray, solution or gel.

In a further preferred embodiment, the transmucosal pharmaceutical composition includes a tocotrienol rich vitamin E fraction, wherein the alpha tocopherol component makes up no more than about 10% of the vitamin E fraction.

In a further preferred embodiment the disease or condition is selected from the group consisting of post exercise muscle soreness, delayed onset muscle soreness, cardiac fibrosis, hypertension, inflammation, stroke, cancer, elevated cholesterol and/or triglycerides, baldness, and a condition resulting from radiation exposure.

The present invention further relates to the use of a transmucosal pharmaceutical composition including at least one tocotrienol or derivative thereof for improving exercise endurance in an animal.

The present invention further relates to the use of a transmucosal pharmaceutical composition including at least one tocotrienol or derivative thereof for promoting weight loss in an animal.

The present invention further relates to the use of a transmucosal pharmaceutical composition including at least one tocotrienol or derivative thereof for stabilizing and/or controlling blood glucose levels in an animal.

Throughout this specification and claims, except with the context requires otherwise, the terms "comprise", "comprises", "comprising" and "comprised" are not intended to exclude further components, integers or steps.

Reference to any prior art in the specification is not, and should not be taken as an acknowledgement or any form of suggestion that this prior art forms part of the common general knowledge in any jurisdiction, or that this prior art could reasonably be expected to be ascertained, understood and regarded as relevant by a person skilled in the art.

DETAILED DESCRIPTION OF THE INVENTION

Figure 1:
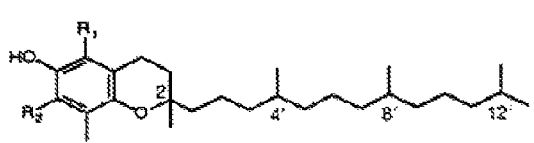
FIG. 1: Shows the structure of the most common tocopherols and tocotrienols. The only difference between main tocotrienols and tocopherols is that the former have an unsaturated isoprenoid tail. In addition to the structures shown here, there are some novel tocotrienols which have been isolated from eg. Kiwi fruit.
Figure 1:
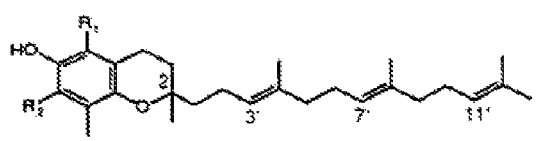

The present inventors have surprisingly found that the transmucosal delivery of tocotrienols results in an enhanced bioavailability and efficacy of the tocotrienols over oral delivery.

Transmucosal and particularly sublingual delivery of the tocotrienols avoids first pass degradation of the tocotrienols by the liver, thereby increasing uptake of the tocotrienols into target tissues, including skeletal muscle, adipose tissue, pancreas, heart and brain, as well as liver, and endothelial tissue of blood vessels.

A number of factors may affect the suitability of transmucosal (such as sublingual) delivery for particular compounds including but not limited to the lipophilicity of the compound of interest and whether the compound has a favourable oil-to-water partition coefficient. An oil-water partition coefficient range of 40 to 2000 is considered optimal for the sublingual delivery of a drug. Given that tocotrienols are highly lipophilic, the delivery of tocotrienols through the transmucosal route and particularly the sublingual route (where all membranes are coated with an aqueous salivary/mucosal layer that would be a barrier to contact and entry) would not have been a method of delivery considered feasible prior to the development of the current invention.

The tocotrienols, or derivatives thereof, that can be used in the compositions and methods of the present invention include naturally occurring tocotrienols (extracted from natural sources) and synthetic tocotrienols. Naturally occurring tocotrienols include alpha, beta, gamma and delta tocotrienols. While naturally occurring tocotrienols are known to exist in only one stereoisomeric form, other stereoisomers may be produced synthetically.

Derivatives of tocotrienols include, but are not limited to; esters, amides, phosphorylated, nitrosylated and succinate/seleno-succinate forms of tocotrienols.

The tocotrienols, or derivatives thereof, used in the composition and methods of the present invention may be extracted from natural sources or synthesised according to methods known in the art. The tocotrienols may be derived from plant extracts such as palm oil, rice bran oil, wheat germ, barley and annatto bean. In a preferred embodiment, the tocotrienols are derived from palm oil or annatto.

The compositions of the present invention may include one form of tocotrienol, or derivative thereof, or a mixture of different tocotrienols, or derivatives thereof.

The tocotrienols in the composition of the present invention may be isolated from other components of a vitamin E extract, or may be present in combination with other vitamin E components.

In a preferred embodiment, the tocotrienol component in the pharmaceutical composition is greater than the tocopherol component.

The tocotrienols may present in a tocotrienol-rich fraction produced from a vitamin E extract. The tocotrienol-rich fraction may include some alpha tocopherol components from the vitamin E. In a preferred embodiment, the tocotrienol-rich fraction includes not more than about 50%, preferably not more than about 40%, more preferably not more than about 30%, more preferably not more than about 20%, more preferably no more than about 10% alpha tocopherol.

In a preferred embodiment, the composition of the present invention includes less than 10% tocopherol.

In another embodiment, the tocopherol present in a vitamin E extract may be removed, modified such that the competitive activity with tocotrienols has been eliminated or reduced. A person skilled in the art would appreciate that there any number of means by which this could be achieved including but not limited to enzymatic modification (see Torres et al "Enzymatic Modification for Ascorbic Acid and Alpha-Tocopherol Enhances their Stability in Food and Nutritional Application" *The Open Food Science Journal* 2008, 2, 1-9).

In a preferred embodiment, the composition of the present invention includes one or both of gamma-tocotrienol and delta-tocotrienol or derivatives thereof.

Transmucosal delivery refers to the route of administration by passage of a pharmaceutical through a mucus membrane. Transmucosal delivery includes within its scope sublingual; sublabial; buccal and nasal delivery.

Transmucosal delivery is achieved due to the connective tissues beneath the epithelium of transmucosal membranes containing capillaries that have the ability to allow some substances to diffuse through them and allow entry into the venous circulation.

The formulation for transmucosal delivery can be a solid dosage form, such as a tablet, capsule, lozenge or film, a gel, a liquid, an emulsion, a suspension, a spray or an aerosol formulation.

The formulations according to the present invention may include pharmaceutically acceptable excipients or carriers suitable for transmucosal delivery systems. Suitable excipients are described, for example, in the *Handbook of Pharmaceutical Excipients*, Rowe, Raymond C; Sheskey, Paul J; Cook, Walter G; Fenton, Marian E (eds), Pharmaceutical Press. Suitable excipients include, but are not limited to cyclodextrins, ethyl cellulose, microcrystalline cellulose, cross-linked polyvinyl pyrrolidone, dicalcium phosphate, calcium carbonate, silica, methylcellulose, carboxymethyl cellulose, hydroxymethylcellulose, hydroxypropylmethylcellulose, alginates, gelatin, guar gum, gum tragacanth, gum acacia, polyacrylic acid, polymethacrylic acid, polysilicic acid and salts thereof, polylactic acid, polymaleic acid, polyvinyl alcohol, polyethylene glycol, polyvinyl pyrrolidone, nonionic block copolymers, carbomers, polycarbophils, polysorbates and water soluble starches.

Gel formulations may include the excipients carboxymethyl cellulose and polyethylene glycol.

In a preferred embodiment of the present invention the composition is formulated for sublingual delivery of at least one tocotrienol, or a derivative thereof.

There are a number of examples of sublingual delivery methods and suitable carrier systems that may be used for the purposes of delivering tocotrienols for the purposes of this invention, some of which may be found in "An Overview on: Sublingual Route for Systemic Drug Delivery"— International Journal of Research in Pharmaceutical and Biomedical Sciences Vol. 3 (2) April-June 2012 which is hereby incorporated by reference in its entirety. Aspects of the current invention include:

i) Enhancement of the absorption of tocotrienols by formulation in carrier systems designed to aid absorption by transmucosal routes of administration, including but not restricted to oral, buccal, sublingual/sublabial, rectal and nasal; and/or ii) Improved delivery of tocotrienols to tissue targets including through vesicle or nanoparticle formulations, such as self-assembling carrier systems that act like chylomicrons, low density lipoproteins, cubosomes, mesophase, self-assembling amphiphiles and non-self-assembling amphiphiles to increase bioavailability of tocotrienols and minimise their hepatic metabolism; and/or iii) Combination with other agents, such as plant extracts, vitamins (including but not limited to niacin) and minerals, protein and lipid and carbohydrate and drugs that would give a synergistic effect in combination with tocotrienols.

Since tocotrienols have multiple actions, the balance between i) and ii) can be adjusted according to the desired therapeutic action. For example, if the natriuretic action of gamma-tocotrienol is the therapeutic target, then the formulation would include gamma tocotrienol alone, or together with tocopherol, which are both metabolized to 2,7,8-trimethyl-2-(b-carboxyethyl)-6-hydroxychroman (gamma-CEHC), which acts on the kidney to increase sodium excretion.

There is growing recognition that reducing the alpha-tocopherol in the diet or supplementary intake is important to reduce interference of the cholesterol-lowering effect of tocotrienols, especially gamma- and delta-tocotrienols. A study in chickens revealed that there was a greater reduction in lipid parameters (including cholesterol production) in birds administered a minimal amount of alpha-tocopherol relative to tocotrienol. In contrast, birds administered the highest amount of alpha-tocopherol had an increase in cholesterol production (Qureshi et al. "Dietary alpha-tocopherol attenuates the impact of gamma-tocotrienol on hepatic 3-hydroxy-3-methylglutaryl coenzyme A reductase activity in chickens" *J Nutrition* 1996 February; 126(2):389-94). A separate study confirmed that high levels of alpha-tocopherol increase cholesterol production (Khor et al "Lipidaemic effects of tocotrienols, tocopherols and squalene: studies in the hamster" *Asia Pacific J Clin Nutr* (1997)6(1): 36-40). Alpha-tocopherol interference with tocotrienol absorption was also described previously by Ikeda et al., who showed that alpha-tocopherol interfered with absorption of alpha-tocopherol, but not gamma-tocotrienol (Ikeda et al "Dietary alpha-tocopherol decreases alpha tocotrienol but not gamma-tocotrienol concentration in rats" *J Nutr* 2003 February; 133(2):428-34). More recently, Japanese researchers found that tocopherols, and alpha-tocopherol in particular, interfered with delta-tocotrienol's ability to induce apoptosis in cancer cells, while blocking the absorption of delta-tocotrienol (Shibata et al "alpha-Tocopherol attenuates the cytotoxic effect of delta-tocotrienol in human colorectal adenocarcinoma cells" *Biochem. Biophys. Res. Commun.* 397(2):214-9. Finally, alpha-tocopherol was shown to interfere with tocotrienols by increasing their catabolism (Sontag et al "influence of major structural features of tocopherols and tocotrienols on their omega oxidation by tocopherol-omega hydroxylase" *J. Lipid Res.* 48(5):1090-8).

It should be understood that included within the scope of the current invention are therapeutics comprising one or more tocotrienols, or derivatives thereof, and which either:
(a) contain no tocopherols;
(b) contain levels of tocopherols that have been minimised as far as practicable; or
(c) contain tocopherols that have been modified so as to ensure that any interference of tocopherol with tocotrienol is either reduced or removed.

Similarly, combination therapies that may yield synergistic effects with tocotrienols are included. For example, using i) and iii), gamma or delta-tocotrienol may be combined with a fibrate drug (which are themselves amphiphilic) in a self-assembling carrier system(s) designed for sublingual absorption. This may bypass hepatic metabolism of tocotrienols and avoid one of the key side-effects of fibrates, which is stomach upset. The combined effect may then be lowering of cholesterol biosynthesis (reduction in HMG-CoA reductase) by the tocotrienol and increase in HDL+ reduction in triglycerides by the fibrate (acting via PPAR-alpha).

The tocotrienols in the compositions of the present invention may be associated with amphiphilic chemicals (including those that self-assemble into molecular structures like cubosomes and mesophases) that enhance sublingual absorption. In particular, the tocotrienols may be associated with self-assembling amphiphilic chemicals that assemble into structures known as cubosomes. Assembly of tocotrienols into cubosomes may also inhibit metabolic degradation of tocotrienols. Cubosomes are bicontinuous cubic liquid crystalline materials that allow for the simultaneous incorporation of water- and oil-soluble materials as well as amphiphiles. The use of cubosomes may enhance the bioavailability of the tocotrienols and allow for the tocotrienols to bypass the liver, which can interfere with delivery of tocotrienols.

Cubosomes may be characterized as having high internal surface area along with cubic crystalline structures and also comprise advantages like simple preparation method, biodegradability of lipids, the ability of encapsulating hydrophobic, hydrophilic, amphiphilic substances, targeting along with controlled release of bioactive agents. The preparation of cubosomes typically involves the emulsification of monoglycerides along with a polymer accompanied via sonication and homogenization. Alternative methods of cubosome preparation known in the art may be also employed.

The composition of the present invention may also include solid lipid core nanoparticles in the formulation, which act as chylomicrons to enhance absorption of lipids from the intestinal tract into the lymphatic system, bypassing the liver (Paliwal, R et al "Effect of lipid core material on characteristics of solid lipid nanoparticles designed for oral lymphatic delivery", Nanomedicine: Nanotechnology, Biology and Medicine 5 (2009) 184-191).

The scope of the invention also contemplates carrier systems such as synthetic nano-low density lipoprotein (Nikanjam, 2006). Such systems allow for delivery of lipophilic drugs via the LDL-receptor of cells, thereby enhancing uptake into body tissues without the need for repackaging and export by the liver in natural lipoproteins.

In one embodiment of the current invention, the tocotrienol or derivative thereof may be formulated as a sublingual or buccal dosage form adapted from the formulations described in Australian Patent Application No. 2010262738 (Cumming et al).

In another embodiment, the composition of the present invention includes at least one tocotrienol or derivative thereof formulated into vesicles or particles such as liposomes, niosomes, transfersomes, pharmacosomes, and nanoparticles. Such vesicles and particles include, but are not limited to those described in Gangwar, M. et al "Recent Advances in various emerging vesicular systems: An overview", Asia Pacific Journal of Tropical Biomedicine (2012) S1176-S1188, Paliwal, R et al (2009), and Sagnella, S. M. et al "Anandamide and analogous endocannabinoids: a lipid self-assembly study", Soft Matter, 2011, 7, 5319, and Hood, E. et al "Nanocarriers for vascular delivery of antioxidants", Nanomedicine (Lond). 2011 September; 6(7): 1257-1272, and Gupta, S. et al "Polyether based amphiphiles for delivery of active components", Polymer 53 (2012) 3053-3078 which are hereby incorporated by reference in their entirety.

The transmucosal tocotrienol composition of the present invention may be produced by the method described in WO 2012/109694 (Ko. Sai, Ying), which is hereby incorporated by reference in its entirety. From the disclosure of Ko, it would appear that the water soluble components within the disclosed compositions and formulations dissolve when contacted with saliva resulting in the generation of micropores on the coating surface which facilitate disintegration of the microcapsules into a liquid gel. The gel lines the mucosal surface thereby delivering the active component and optimising absorption. Further, Ko showed that this sub-lingual delivery platform can transport molecules such as proteins, which comprise both hydrophilic and hydrophobic moieties, across the sub-lingual mucosa.

The composition of the present invention may include tocotrienols, beta-cyclodextrin (and/or other cyclodextrin variants) in appropriate ratios so as to host tocotrienols in the hydrophobic core of the cyclodextrin molecule. An example of this formulation is found in the work by Mannila J, Jarvinen T, Jarvine K & Jarho P, "Precipitation complexation method produces cannabidiol/beta cyclodextrin inclusion complex suitable for sublingual administration on cannabidiol" Journal of Pharmaceutical Sciences 96, 312-319, 2007. Tocotrienols are known to form complexes with gamma-cyclodextrin, but this formulation is unsuitable due to the degradation of the gamma-cyclodextrin by salivary amylase, whereas alpha and beta forms are resistant (Ikeda S, Uchida T, Ichikawa T et al, "Complexation of tocotrienol with gamma-cyclodextrin enhances intestinal absorption of tocotrienols in rats" Bioscience, Biotechnology and Biochemistry 74, 1453-1457, 2010).

Any number of formulations and compositions may be employed for the purposes of performing the current invention, provided that said compositions and formulations comprise pharmaceutically acceptable excipients and carriers that, when exposed to the aqueous/salivary mucosal environment, will allow for the tocotrienols present in the composition to remain in contact with the mucosal surface for a sufficient period of time to allow for absorption, facilitate, or at least not impede, the absorption of the tocotrienols through the mucosal membrane and allow for the tocotrienols to be absorbed in a bioavailable form.

In another embodiment, the transmucosally administered tocotrienol may be combined with any other compound that will complement and enhance the therapeutic effect of the tocotrienol, or derivative thereof, including, but not limited to, monoglycerides, lignans isoprenoids, amino acids, CoQ10, polyphenols, omega-3 fatty acids, endocannabinoid system agonists and antagonists, flavonoids, carotenoids, mono and oligosaccharides, niacin and bioactive peptides.

In another embodiment, the transmucosally administered tocotrienol may be combined with extracts from sesame seeds and or sesame lignands.

It is also understood that derivatives of tocotrienols that enhance the therapeutic effect are also included, such as phosphorylated, nitrosylated and succinate/seleno-succinate forms.

One example of a method of modifying tocotrienols can be found in Vraka et al "Synthesis and study of the cancer cell growth inhibitory properties of α-, γ-tocopheryl and γ-tocotrienyl 2-phenylselenyl succinates" Bioorganic & Medicinal Chemistry 14 (2006) 2684-2696, which is hereby incorporated by reference in its entirety.

In a further embodiment the tocotrienol (and/or its derivatives), is administered in the form of a pharmaceutical composition suitable for buccal, sub-lingual, mucosal or nasal administration, though preferably sublingual administration, in combination with a further compound designed to complement and enhance the therapeutic effect of the tocotrienol, or derivative thereof, selected from the group consisting of: monoglycerides; lignans; isoprenoids; polyphenols; flavonoids; carotenoids; mono and oligosaccharides; niacin and bioactive peptides.

In another embodiment, tocotrienol (and/or its derivatives) is administered in the form of a pharmaceutical composition suitable for buccal, sub-lingual, mucosal or nasal administration, preferably sublingual administration, and wherein tocopherol is absent or, if tocopherol is present, the interfering and/or competitive activity (in relation to tocotrienol) of any tocopherol present in said pharmaceutical composition has been eliminated, reduced or minimized. Said composition may include, or be administered in combination with any other compound such as monoglycerides, lignans isoprenoids, polyphenols, flavonoids, carotenoids, mono and oligosaccharides, niacin and bioactive peptides that will complement and enhance the therapeutic effect of tocotrienols. Orally ingested tocotrienols have a lower bioavailability than orally ingested tocopherols, as shown by reduced peak concentrations in plasma following ingestion and shorter half-lives in a recent human study (S, Fairus, S. et al Nutr J. 2012 Jan. 17; 11:5). An animal study has estimated oral bioavailability to be 4× lower for tocotrienols compared to tocopherol (9% vs 36%) (Abuasal, B S. et al Biopharm Drug Dispos. 2012 July; 33(5):246-56). The mechanisms that determine the bioavailability of tocotrienols have not been fully elucidated, but intestinal absorption and hepatic processing appear to be key factors.

Absorption of vitamin E isomers varies between individuals, perhaps due to differences in expression of different transporters such as Scavenger Receptor B1 and the Niemann-Pick C1L1 receptor, as well as the presence of other lipids that share these transport mechanisms, such as cholesterol (Reboul, E. and Borel, P. Prog Lipid Res 2011 50:388-402). Hepatic processing is another source of biodiscrimination between tocopherol and tocotrienol isomers, on the basis of differences in affinity for the intracellular alpha-tocopherol transport protein (a-TTP). The relative affinity of vitamin E isomers towards a-TTP has been demonstrated to be in the order of alpha-tocopherol (100%)>alpha-tocotrienol (12%)>gamma-tocotrienol (9%)>delta-tocopherol (2%) (Hosomi, A. et al FEBS Letters 1997, 409:105-108). This mechanism helps to explain the occurrence of alpha-tocopherol as the major vitamin E isomer detected in triglyceride-rich particles, low density and high density lipoproteins, and the rapid disappearance of alpha-tocotrienol, gamma-tocotrienol and delta-tocotrienol from circulating plasma and lipoproteins. In humans, plasma concentrations of alpha-tocotrienol were 2-fold higher than that of gamma-tocotrienol, and almost 10 times higher than delta-tocotrienol after supplementation with the same dose of tocotrienol preparations (O'Byrne, D. et al Free Radic Biol Med 2000, 29:834-845).

Without wishing to be bound by theory, sublingual delivery of tocotrienols, or derivatives thereof, according to the current invention is believed to have at least two distinct advantages compared to traditional oral delivery. Firstly, it may overcome the problem of low intestinal absorption of tocotrienols by ensuring high absorption via the sublingual lymphatic system. This technique will also bypass the low affinity of tocotrienols for the alpha-tocopherol transport protein, because the lymphatic circulation will deliver them to the target tissues, without the necessity for incorporation by the liver into triglyceride, and lipoproteins and export into the circulation. This method will also minimise first-pass metabolism of tocotrienols by the liver and increase the amount of tocotrienols delivered to other organs.

Moreover, by using the sublingual delivery system in combination with other techniques, such as assembling tocotrienols into nanoparticles either in their natural form or as chemical derivatives, or in combination with other molecules (Abuasal, B. S. et al Lipids. 2012 May; 47(5):461-9. doi: 10.1007/s11745-012-3655-4. Epub 2012 Jan. 24), the delivery and the bioactivity can be tuned to particular target tissues and therapeutic applications. Accordingly, in a further embodiment, the composition of the present invention includes tocotrienol, or derivative thereof, assembled into nanoparticles.

The inventors of the present application have confirmed a previous study (Lee, S. P., Mar, G. Y. & Ng, L. T. 2009, *European Journal of Applied Physiology,* 107, 587-595.) that tocotrienols can improve exercise endurance in in normal weight Wistar rats, by showing that this improvement also extends to Sprague-Dawley rats with diet-induced obesity. Furthermore, the inventors of the present application have demonstrated a surprising increase in efficacy of a sublingual formulation of tocotrienol over an oral formulation in improving exercise endurance in humans.

Accordingly, in another aspect the present invention provides a method of improving exercise endurance and performance in an animal, and in particular a human, through the administration of tocotrienol (and/or its derivatives) in the form of a pharmaceutical composition suitable for buccal, sub-lingual, mucosal or nasal administration, preferably sub-lingual administration.

In another aspect, the present invention provides a method of improving exercise endurance and performance in animals, and in particular humans through the administration of tocotrienol (and/or its derivatives) in the form of a pharmaceutical composition suitable for buccal, sub-lingual, mucosal or nasal administration, preferably sub-lingual administration, in combination with any other compound such as monoglycerides, lignans isoprenoids, polyphenols, flavonoids, carotenoids, mono and oligosaccharides, niacin and bioactive peptides that will complement and enhance the effect of tocotrienols with respect to improvement in exercise endurance.

In another aspect, the present invention provides a method of improving exercise endurance and performance in animals, and in particular humans through the administration of tocotrienol (and/or its derivatives) in the form of a pharmaceutical composition suitable for buccal, sub-lingual, mucosal or nasal administration, though preferably sub-lingual administration, and wherein the tocotrienol component is greater than the tocopherol component, or tocopherol is absent or, if tocopherol is present, the interfering and/or competitive activity of any tocopherol present in said pharmaceutical composition has been eliminated, reduced or minimized. Said composition may include, or be administered in combination with, any other compound such as monoglycerides, lignans isoprenoids, polyphenols, flavonoids, carotenoids, mono and oligosaccharides, niacin and bioactive peptides that will complement and enhance the effect of tocotrienols with respect to improvement in exercise endurance.

In another aspect, the present invention provides a method of promoting weight loss in animals, and in particular humans through the administration of tocotrienol (and/or its derivatives) is in the form of a pharmaceutical composition suitable for buccal, sub-lingual, mucosal or nasal administration, though preferably sub-lingual administration.

In another aspect, the present invention provides a method of promoting weight loss in animals, and in particular humans through the administration of tocotrienol (and/or its derivatives) is in the form of a pharmaceutical composition suitable for buccal, sub-lingual, mucosal or nasal administration, though preferably sub-lingual administration, in combination with any other compound such as monoglycerides, lignans isoprenoids, polyphenols, flavonoids, carotenoids, mono and oligosaccharides, niacin and bioactive peptides that will complement and enhance the effect of tocotrienols with respect to promoting weight loss.

In another aspect, the present invention provides a method of promoting weight loss in animals, and in particular humans through the administration of tocotrienol (and/or its derivatives) in the form of a pharmaceutical composition suitable for buccal, sub-lingual, mucosal or nasal administration, though preferably sub-lingual administration, and wherein the tocotrienol component is greater than the tocopherol component, or tocopherol is absent or, if tocopherol is present, the interfering and/or competitive activity of any tocopherol present in said pharmaceutical composition has been eliminated, reduced or minimized. Said composition may include, or be administered in combination with, any other compound such as monoglycerides, lignans isoprenoids, polyphenols, flavonoids, carotenoids, mono and oligosaccharides, niacin and bioactive peptides that will complement and enhance the effect of tocotrienols with respect to promotion of weight loss.

Tocotrienols have been shown to improve control of blood glucose and insulin response (Kuhad et al (2009)).

Accordingly, in another aspect, the present invention provides a method of stabilizing and/or controlling blood glucose levels in animals, and in particular humans through the administration of tocotrienol (and/or its derivatives) is in the form of a pharmaceutical composition suitable for buccal, sub-lingual, mucosal or nasal administration, though preferably sub-lingual administration.

In another aspect, the present invention provides a method of stabilizing and/or controlling blood glucose levels in animals, and in particular humans through the administration of tocotrienol (and/or its derivatives) is in the form of a pharmaceutical composition suitable for buccal, sub-lingual, mucosal or nasal administration, though preferably sub-lingual administration, in combination with any other compound such as monoglycerides, lignans isoprenoids, polyphenols, flavonoids, carotenoids, mono and oligosaccharides, niacin and bioactive peptides that will complement and enhance the effect of tocotrienols with respect to stabilizing and/or controlling blood glucose levels.

In another aspect, the present invention provides a method of stabilizing and/or controlling blood glucose levels in animals, and in particular humans through the administration of tocotrienol (and/or its derivatives) in the form of a pharmaceutical composition suitable for buccal, sub-lingual, mucosal or nasal administration, though preferably sub-lingual administration, and wherein the tocotrienol component is greater than the tocopherol component or, tocopherol is absent or tocopherol is absent or, if tocopherol is present, the interfering and/or competitive activity of any tocopherol present in said pharmaceutical composition has been eliminated, reduced or minimized. Said composition may include, or be administered in combination with, any other compound such as monoglycerides, lignans isoprenoids, polyphenols, flavonoids, carotenoids, mono and oligosaccharides, niacin and bioactive peptides that will complement and enhance the effect of tocotrienols with respect to stabilizing and/or controlling blood glucose levels.

In another aspect, the present invention provides a method of reducing hypertension in animals, and in particular humans through the administration of tocotrienol (and/or its derivatives) is in the form of a pharmaceutical composition suitable for buccal, sub-lingual, transdermal, oral, mucosal or nasal administration, though preferably sub-lingual administration.

In another aspect, the present invention provides a method of reducing hypertension in animals, and in particular humans through the administration of tocotrienol (and/or its derivatives) is in the form of a pharmaceutical composition suitable for buccal, sub-lingual, mucosal or nasal administration, though preferably sub-lingual administration, in combination with any other compound such as monoglycerides, lignans isoprenoids, polyphenols, flavonoids, carotenoids, mono and oligosaccharides, niacin and bioactive peptides that will complement and enhance the effect of tocotrienols with respect to reducing hypertension.

In another aspect, the present invention provides a method of reducing hypertension in animals, and in particular humans through the administration of tocotrienol (and/or its derivatives) in the form of a pharmaceutical composition suitable for buccal, sub-lingual, mucosal or nasal administration, though preferably sub-lingual administration, and wherein the tocotrienol component is greater than the tocopherol component or, tocopherol is absent or, if tocopherol is present, the interfering and/or competitive activity of any tocopherol present in said pharmaceutical composition has been eliminated, reduced or minimized. Said composition may include, or be administered in combination with, any other compound such as monoglycerides, lignans isoprenoids, polyphenols, flavonoids, carotenoids, mono and oligosaccharides, niacin and bioactive peptides that will complement and enhance the effect of tocotrienols with respect to reducing hypertension.

In another aspect, the present invention provides a method of treating ischemic disease in animals, and in particular humans through the administration of tocotrienol (and/or its derivatives) in the form of a pharmaceutical composition suitable for buccal, sub-lingual, mucosal or nasal administration, though preferably sub-lingual administration.

In another aspect, the present invention provides a method of treating ischemic disease in animals, and in particular humans through the administration of tocotrienol (and/or its derivatives) in the form of a pharmaceutical composition suitable for buccal, sub-lingual, mucosal or nasal administration, though preferably sub-lingual administration, in combination with any other compound such as monoglycerides, lignans isoprenoids, polyphenols, flavonoids, carotenoids, mono and oligosaccharides, niacin and bioactive peptides that will complement and enhance the effect of tocotrienols with respect to treating ischemic disease.

In another aspect, the present invention provides a method of treating ischemic disease in animals, and in particular humans through the administration of tocotrienol (and/or its derivatives) in the form of a pharmaceutical composition suitable for buccal, sub-lingual, mucosal or nasal administration, though preferably sub-lingual administration, and wherein the tocotrienol component is greater than the tocopherol component or, tocopherol is absent or, if tocopherol is present, the interfering and/or competitive activity of any tocopherol present in said pharmaceutical composition has been eliminated, reduced or minimized. Said composition may include, or be administered in combination with, any other compound such as monoglycerides, lignans isoprenoids, polyphenols, flavonoids, carotenoids, mono and oligosaccharides, niacin and bioactive peptides that will complement and enhance the effect of tocotrienols with respect to treating ischemic disease.

In another aspect, the present invention provides a method of reducing cholesterol and/or triglycerides in animals, and in particular humans through the administration of tocotrienol (and/or its derivatives) in the form of a pharmaceutical composition suitable for buccal, sub-lingual mucosal or nasal administration, though preferably sub-lingual administration.

In another aspect, the present invention provides a method of reducing cholesterol and/or triglycerides in animals, and in particular humans through the administration of tocotrienol (and/or its derivatives) in the form of a pharmaceutical composition suitable for buccal, sub-lingual, mucosal or nasal administration, though preferably sub-lingual administration, in combination with any other compound such as monoglycerides, lignans isoprenoids, polyphenols, flavonoids, carotenoids, mono and oligosaccharides, niacin and bioactive peptides that will complement and enhance the effect of tocotrienols with respect to reducing cholesterol and/or triglycerides.

In another aspect, the present invention provides a method of reducing cholesterol and/or triglycerides in animals, and in particular humans through the administration of tocotrienol (and/or its derivatives) in the form of a pharmaceutical composition suitable for buccal, sub-lingual, mucosal or nasal administration, though preferably sub-lingual administration, and wherein the tocotrienol component is greater than the tocopherol component or, tocopherol is absent or, if tocopherol is present, the interfering and/or competitive activity of any tocopherol present in said pharmaceutical composition has been eliminated, reduced or minimized. Said composition may include, or be administered in combination with, any other compound such as monoglycerides, lignans isoprenoids, polyphenols, flavonoids, carotenoids, mono and oligosaccharides, niacin and bioactive peptides that will complement and enhance the effect of tocotrienols with respect to reducing cholesterol and/or triglycerides.

In another aspect, the present invention provides a method of treating cancer in animals, and in particular humans through the administration of tocotrienol (and/or its derivatives) in the form of a pharmaceutical composition suitable for buccal, sub-lingual, transdermal, oral, mucosal or nasal administration, though preferably sub-lingual administration.

In another aspect, the present invention provides a method of treating cancer in animals, and in particular humans through the administration of tocotrienol (and/or its derivatives) in the form of a pharmaceutical composition suitable for buccal, sub-lingual, mucosal or nasal administration, though preferably sub-lingual administration, in combination with any other compound such as monoglycerides, lignans isoprenoids, polyphenols, flavonoids, carotenoids, mono and oligosaccharides, niacin and bioactive peptides that will complement and enhance the effect of tocotrienols with respect to treating cancer.

In another aspect, the present invention provides a method of treating cancer in animals, and in particular humans through the administration of tocotrienol (and/or its derivatives) in the form of a pharmaceutical composition suitable for buccal, sub-lingual, mucosal or nasal administration, and wherein the tocotrienol component is greater than the tocopherol component or, tocopherol is absent or, if tocopherol is present, the interfering and/or competitive activity of any tocopherol present in said pharmaceutical composition has been eliminated, reduced or minimized.

Said composition may include, or be administered in combination with, any other compound such as monoglycerides, lignans isoprenoids, polyphenols, flavonoids, carotenoids, mono and oligosaccharides, niacin and bioactive peptides that will complement and enhance the effect of tocotrienols with respect to treating cancer.

In another aspect, the present invention provides a method of treating cancer in animals, and in particular humans through the administration of tocotrienol (and/or its derivatives) in the form of a pharmaceutical composition suitable for buccal, sub-lingual, mucosal or nasal administration, though preferably sub-lingual administration.

In another aspect, the present invention provides a method of increasing the bioavailability of tocotrienols administered to animals, and in particular humans through the administration of tocotrienol (and/or its derivatives) in the form of a pharmaceutical composition suitable for buccal, sub-lingual, mucosal or nasal administration, though preferably sub-lingual administration, in combination with any other compound such as monoglycerides, lignans isoprenoids, polyphenols, flavonoids, carotenoids, mono and oligosaccharides, niacin and bioactive peptides that will complement and enhance the effect of tocotrienols with respect to increasing the bioavailability of tocotrienols administered to animals.

In another aspect, the present invention provides a method of increasing the bioavailability of tocotrienols administered to animals, and in particular humans through the administration of tocotrienol (and/or its derivatives) in the form of a pharmaceutical composition suitable for buccal, sub-lingual, mucosal or nasal administration, though preferably sub-lingual administration, and wherein the tocotrienol component is greater than the tocopherol component, tocopherol is absent or, if tocopherol is present, the interfering and/or competitive activity of any tocopherol present in said pharmaceutical composition has been eliminated, reduced or minimized. Said composition may include, or be administered in combination with, any other compound such as monoglycerides, lignans isoprenoids, polyphenols, flavonoids, carotenoids, mono and oligosaccharides, niacin and bioactive peptides that will complement and enhance the effect of tocotrienols with respect to increasing the bioavailability of tocotrienols administered to animals.

In another aspect, the present invention provides a method of minimizing the dosage required to achieve a therapeutic effect by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration.

In another aspect, the present invention provides a method of minimizing the dosage required to achieve a therapeutic effect by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration, in combination with any other compound such as monoglycerides, lignans isoprenoids, polyphenols, flavonoids, carotenoids, mono and oligosaccharides, niacin and bioactive peptides that will complement and enhance the effect of tocotrienols with respect to minimizing the dosage required to achieve a therapeutic effect by the administration of tocotrienols.

In another aspect, the present invention provides a method of minimizing the dosage required to achieve a therapeutic effect by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration, and wherein the tocotrienol component is greater than the tocopherol component or, tocopherol is absent or, if tocopherol is present, the interfering and/or competitive activity of any tocopherol present in said pharmaceutical composition has been eliminated, reduced or minimized.

Said composition may include, or be administered in combination with, any other compound such as monoglycerides, lignans isoprenoids, polyphenols, flavonoids, carotenoids, mono and oligosaccharides, niacin and bioactive peptides that will complement and enhance the effect of tocotrienols with respect to minimizing the dosage required to achieve a therapeutic effect by the administration of tocotrienols.

In another aspect, the present invention provides a method of reducing and/or inhibiting inflammation by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration.

In another aspect, the present invention provides a method of reducing or inhibiting inflammation by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration, in combination with any other compound such as monoglycerides, lignans isoprenoids, polyphenols, flavonoids, carotenoids, mono and oligosaccharides, niacin and bioactive peptides that will complement and enhance the effect of tocotrienols with respect to reducing and/or inhibiting inflammation by the administration of tocotrienols.

In another aspect, the present invention provides a method of reducing and/or inhibiting inflammation by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration, and wherein the tocotrienol component is greater than the tocopherol component or, tocopherol is absent or, if tocopherol is present, the interfering and/or competitive activity of any tocopherol present in said pharmaceutical composition has been eliminated, reduced or minimized. Said composition may include, or be administered in combination with, any other compound such as monoglycerides, lignans isoprenoids, polyphenols, flavonoids, carotenoids, mono and oligosaccharides, niacin and bioactive peptides that will complement and enhance the effect of tocotrienols with respect to reducing and/or inhibiting inflammation by the administration of tocotrienols.

In another aspect, the present invention provides a method of reducing and/or inhibiting post exercise muscle soreness by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration.

In another aspect, the present invention provides a method of reducing and/or inhibiting post exercise muscle soreness by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration, in combination with any other compound such as monoglycerides, lignans isoprenoids, polyphenols, flavonoids, carotenoids, mono and oligosaccharides, niacin and bioactive peptides that will complement and enhance the effect of tocotrienols with respect to reducing and/or inhibiting post exercise muscle soreness by the administration of tocotrienols.

In another aspect, the present invention provides a method of reducing and/or inhibiting post exercise muscle soreness by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration, and wherein the tocotrienol component is greater than the tocopherol component or, tocopherol is absent or, if tocopherol is present, the interfering and/or competitive activity of any tocopherol present in said pharmaceutical composition has been eliminated, reduced or minimized. Said composition may include, or be administered in combination with, any other compound such as monoglycerides, lignans isoprenoids, polyphenols, flavonoids, carotenoids, mono and oligosaccharides, niacin and bioactive peptides that will complement and enhance the effect of tocotrienols with respect to reducing and/or inhibiting post exercise muscle soreness by the administration of tocotrienols.

In another aspect, the present invention provides a method of reducing and/or inhibiting delayed onset muscle soreness by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration.

In another aspect, the present invention provides a method of reducing and/or inhibiting delayed onset muscle soreness by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration, in combination with any other compound such as monoglycerides, lignans isoprenoids, polyphenols, flavonoids, carotenoids, mono and oligosaccharides, niacin and bioactive peptides that will complement and enhance the effect of tocotrienols with respect to reducing and/or inhibiting delayed onset muscle soreness by the administration of tocotrienols.

In another aspect, the present invention provides a method of reducing and/or inhibiting delayed onset muscle soreness by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration, and wherein the tocotrienol component is greater than the tocopherol component or, tocopherol is absent or, if tocopherol is present, the interfering and/or competitive activity of any tocopherol present in said pharmaceutical composition has been eliminated, reduced or minimized.

Said composition may include, or be administered in combination with, any other compound such as monoglycerides, lignans isoprenoids, polyphenols, flavonoids, carotenoids, mono and oligosaccharides, niacin and bioactive peptides that will complement and enhance the effect of tocotrienols with respect to reducing and/or inhibiting delayed onset muscle soreness by the administration of tocotrienols.

In another aspect, the present invention provides a method of reducing and/or treating cardiac fibrosis by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration.

In another aspect, the present invention provides a method of reducing and/or treating cardiac fibrosis by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration, in combination with any other compound such as monoglycerides, lignans isoprenoids, polyphenols, flavonoids, carotenoids, mono and oligosaccharides, niacin and bioactive peptides that will complement and enhance the effect of tocotrienols with respect to reducing and/or treating cardiac fibrosis by the administration of tocotrienols.

In another aspect, the present invention provides a method of reducing and/or treating cardiac fibrosis by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration, and wherein the tocotrienol component is greater than the tocopherol component or, tocopherol is absent or, if tocopherol is present, the interfering and/or competitive activity of any tocopherol present in said pharmaceutical composition has been eliminated, reduced or minimized. Said composition may include, or be administered in combination with, any other compound such as monoglycerides, lignans isoprenoids, polyphenols, flavonoids, carotenoids, mono and oligosaccharides, niacin and bioactive peptides that will complement and enhance the effect of tocotrienols with respect to reducing and/or treating cardiac fibrosis by the administration of tocotrienols.

In another aspect, the present invention provides a method of treating radiation exposure in an animal by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration.

In another aspect, the present invention provides a method of treating radiation exposure in an animal by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration, in combination with any other compound such as monoglycerides, lignans isoprenoids, polyphenols, flavonoids, carotenoids, mono and oligosaccharides, niacin and bioactive peptides that will complement and enhance the effect of tocotrienols with respect to treating radiation exposure in an animal by the administration of tocotrienols.

In another aspect, the present invention provides a method of treating radiation exposure in an animal by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration, and wherein the tocotrienol component is greater than the tocopherol component or, tocopherol is absent or, if tocopherol is present, the interfering and/or competitive activity of any tocopherol present in said pharmaceutical composition has been eliminated, reduced or minimized. Said composition may include, or be administered in combination with, any other compound such as monoglycerides, lignans isoprenoids, polyphenols, flavonoids, carotenoids, mono and oligosaccharides, niacin and bioactive peptides that will complement and enhance the effect of tocotrienols with respect to treating radiation exposure in an animal by the administration of tocotrienols.

In another aspect, the present invention provides a method of treating male pattern baldness by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration.

In another aspect, the present invention provides a method of treating male pattern baldness by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration, in combination with any other compound such as monoglycerides, lignans isoprenoids, polyphenols, flavonoids, carotenoids, mono and oligosaccharides, niacin and bioactive peptides that will complement and enhance the effect of tocotrienols with respect to treating male pattern baldness by the administration of tocotrienols.

In another aspect, the present invention provides a method of treating male pattern baldness by the administration of tocotrienols to animals, and in particular humans through the administration of tocotrienol (and/or its derivatives) in the form of a pharmaceutical composition suitable for buccal, sub-lingual, mucosal or nasal administration, though preferably sub-lingual administration, and wherein the tocotrienol component is greater than the tocopherol component or, tocopherol is absent or, if tocopherol is present, the interfering and/or competitive activity of any tocopherol present in said pharmaceutical composition has been eliminated, reduced or minimized. Said composition may include, or be administered in combination with, any other compound such as monoglycerides, lignans isoprenoids, polyphenols, flavonoids, carotenoids, mono and oligosaccharides, niacin and bioactive peptides that will complement and enhance the effect of tocotrienols with respect to treating male pattern baldness by the administration of tocotrienols.

The invention is further described with reference to the following non-limiting examples.

EXAMPLES

Example 1

The Effect of Dietary Tocotrienols on Glucose Tolerance, Hypertension, Cardiac Fibrosis and Renal Sodium Excretion in Rats Sprague-Dawley rats were fed a high fat diet (22%) for 8 weeks to induce obesity.

Figure 2:
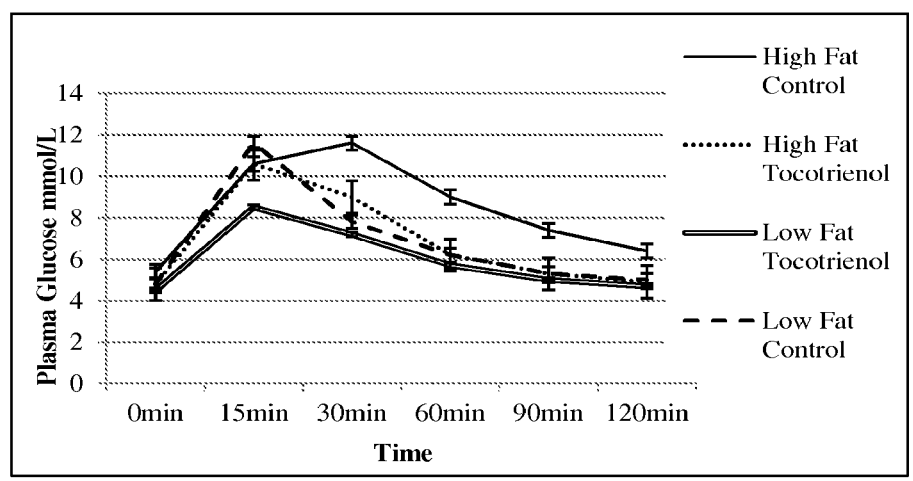
FIG. 2: In Sprague-Dawley rats with obesity induced by feeding a high fat (22%) diet for 8 weeks, dietary tocotrienols (25 mg/kg/d) improved tolerance to a glucose load (2 g/kg, i.p.) compared to animals that did not receive tocotrienols (n=9, p<0.01; Mathai et al, 2011).

As shown in FIG. 2, dietary tocotrienols (25 mg/kg/d) improved tolerance to a glucose load (2 g/kg, i.p.) in obese rats compared to animals that did not receive tocotrienols (n=9, p<0.01; Mathai et al, 2011)

Figure 3:
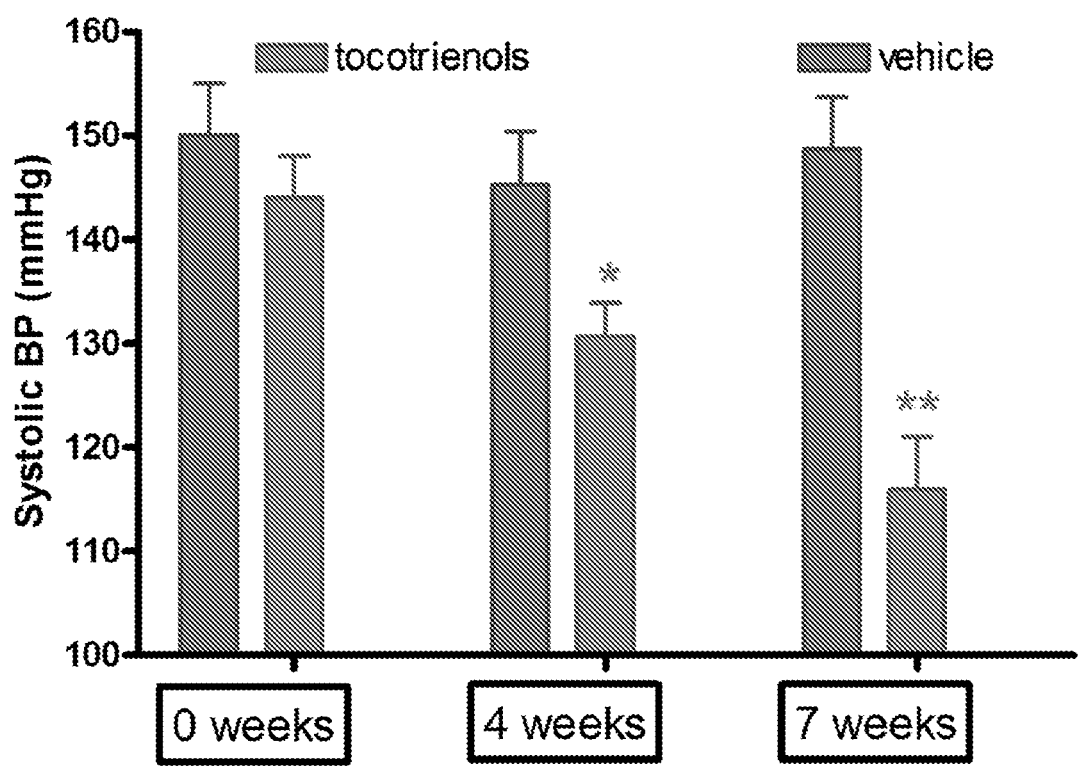
FIG. 3: In Sprague-Dawley rats maintained on a high fat diet for 8 weeks, dietary tocotrienols (50 mg/kg/d) gradually reversed the established hypertension compared to the placebo-control group.
Figure 4:
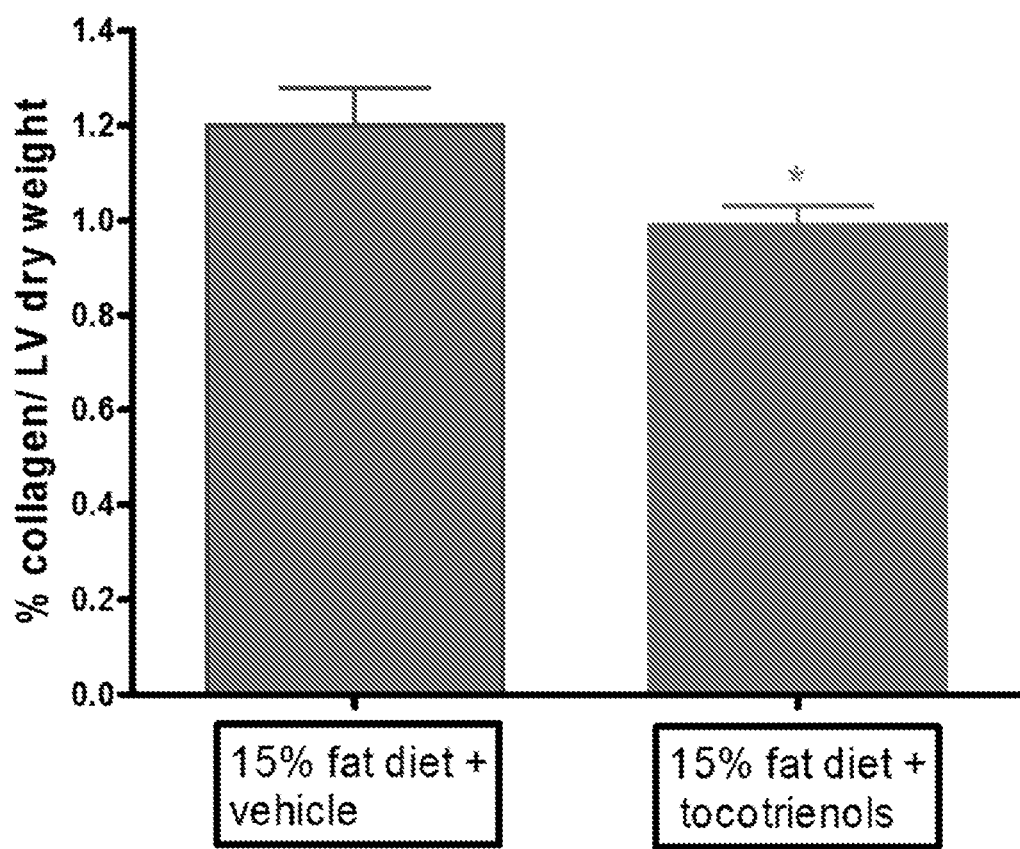
FIG. 4: The reduction in blood pressure observed in FIG. 3 was accompanied by a reduction in cardiac fibrosis, as measured by hydroxyproline content of the left ventricle.

As shown in FIG. 3, dietary tocotrienols (50 mg/kg/d) gradually reversed the established hypertension in obese rats compared to the placebo-control group. Furthermore, as shown in FIG. 4, the reduction in blood pressure observed in FIG. 3 was accompanied by a reduction in cardiac fibrosis, as measured by hydroxyproline content of the left ventricle.

Figure 5:
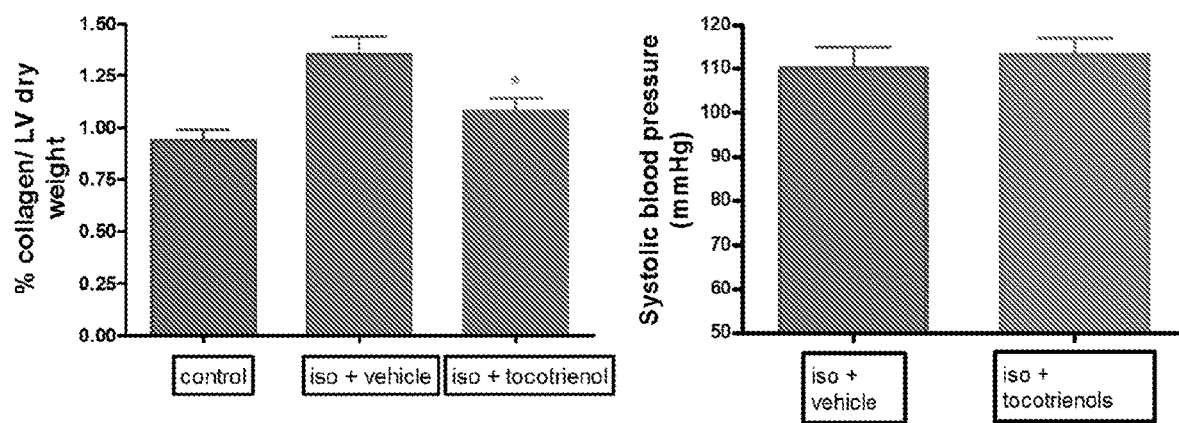
FIG. 5: A separate experiment showed that the cardiac fibrosis induced by isoproterenol was inhibited by tocotrienol supplementation. Since this model of cardiac fibrosis did not increase blood pressure, it shows that the antifibrotic effect of tocotrienols is separate to the antihypertensive effect.

As shown in FIG. 5, cardiac fibrosis induced by isoproterenol was inhibited by tocotrienol supplementation. Since this model of cardiac fibrosis did not increase blood pressure, it shows that the antifibrotic effect of tocotrienols is separate to the antihypertensive effect.

Figure 6:
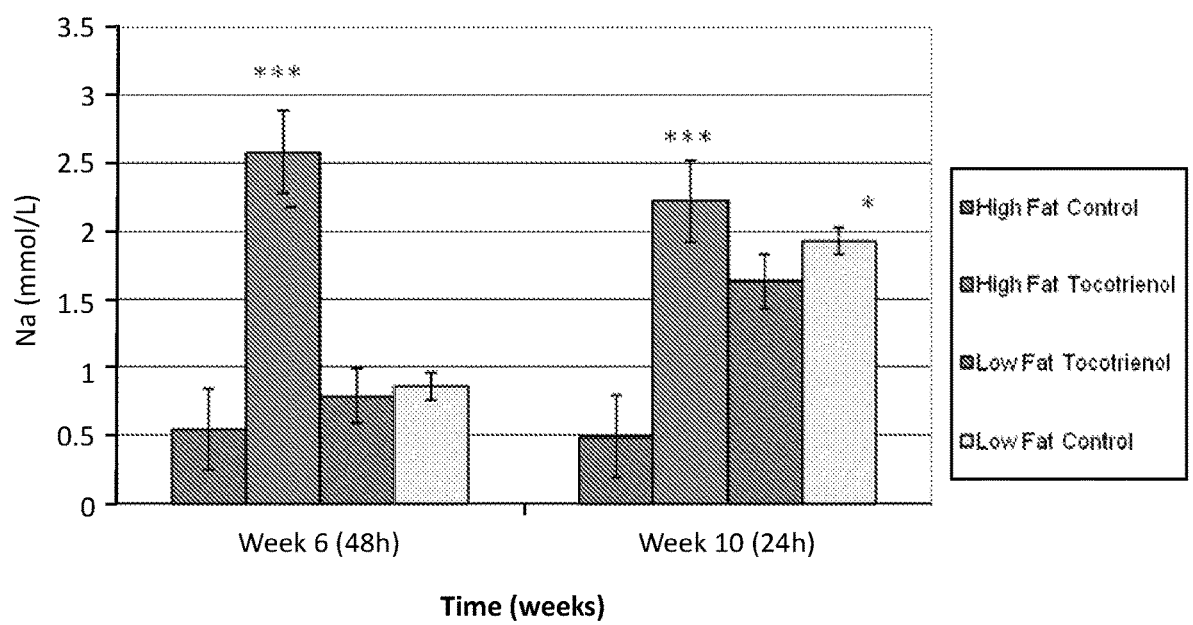
FIG. 6: Dietary supplementation with tocotrienols increased renal sodium excretion in rats fed a high fat diet. This is important as obesity is often accompanied by sodium and water retention that can lead to co-morbidities such as elevated blood volume and pressure and cardiovascular disease.

As shown in FIG. 6, dietary supplementation with tocotrienols increased renal sodium excretion in rats fed a high fat diet. This is important as obesity is often accompanied by sodium and water retention that can lead to co-morbidities such as elevated blood volume and pressure and cardiovascular disease Example 2

Tocotrienol Supplementation Enhances Rat Exercise Capacity

Figure 7:
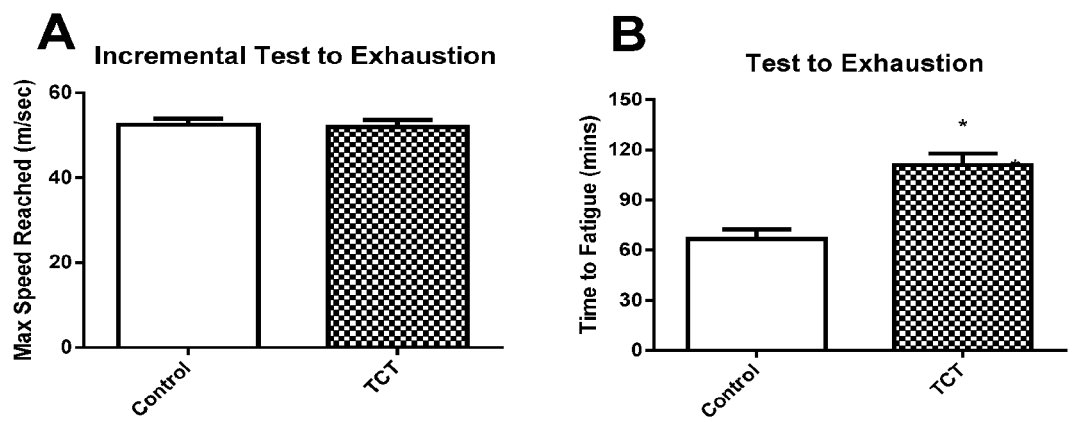
FIG. 7: The effect of tocotrienols on exercise endurance in rats. A: maximum speed to exhaustion in rats administered tocotrienols (TCT) versus control. B: Time to exhaustion in rats administered tocotrienols (TCT) versus control.

Fifteen Sprague-Dawley rats were made obese through 10 weeks feeding on a high-fat diet and then split into a control (n=7) and tocotrienol supplemented group (n=8). As shown in FIG. 7, Supplementation of the diet with a tocotrienol rich fraction nearly doubled the capacity for untrained rats for exercise on a treadmill.

In the first part of this trial, an incremental test to exhaustion was performed to determine the maximum running speed of rates in the control and tocotrienol groups. FIG. 7A shows the average peak velocity reached in Control and tocotrienol-supplemented (50 mg/kg/d) groups performing the incremental test to exhaustion at week 8. This showed that maximum speed was similar between the groups. During this second treadmill run, individual rats ran at 65% of their maximum speed. FIG. 7B shows the average time taken to reach fatigue during the time to exhaustion for the 2 groups at week 10. Data showed as mean±SEM (n=7-8/group). The "*" signifies a statistical significant difference (P<0.05) compared to the Control group.

These results complement previous results which showed that normal Wistar rats more than doubled swim exercise time when fed tocotrienols (Lee, S. P., Mar, G. Y. & Ng, L. T. 2009, "Effects of tocotrienol-rich fraction on exercise endurance capacity and oxidative stress in forced swimming rats", European Journal of Applied Physiology, 107, 587-595.)

Example 3

Tocotrienol Supplementation Enhances Exercise Endurance in Humans

Tocotrienols were formulated into the following sublingual dosage form: A 220 mg sublingual tablet formulation was prepared containing a dose of 10 mg tocotrienol comprised of the actives delta-tocotrienol 9 mg and gamma tocotrienol 1 mg, and the following excipients: dextrose, mannitol, marine gelatin, 1-leucine, 1-arginine, pre-gel starch, PEG-200, propylene glycol, talc, silica dioxide, magnesium stearate, carotenoids.

Four subjects were administered two doses of 20 mg sublingual tocotrienol tablets in the morning and evening for a total of four weeks, with a placebo being administered in the same fashion for an additional period of four weeks thereafter either before or after the tocotrienol treatment.

At the conclusion of each four week period, subjects performed an incremental exercise to exhaustion test on a standard exercise bike that comprised cycling on a stationary bicycle at staged increments of maximal capacity (65%, 70%, 75%, 80%, 85% according to age-adjusted maximal heart rate for each participant). Subjects were equipped with heart rate monitors and Borg ratings of physical exertion (scale of 11-20) were obtained every 5 min during cycling exercise, as well time to exhaustion.

Figure 8:
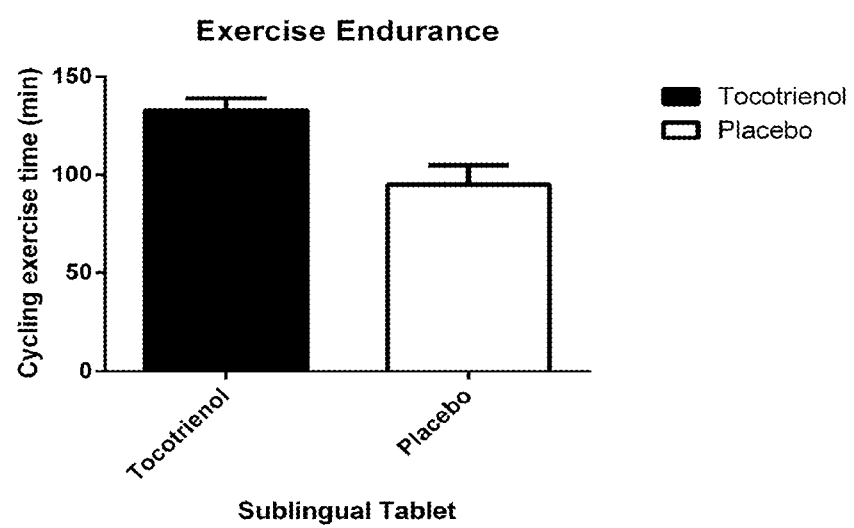
FIG. 8: The effect of tocotrienols on exercise endurance in humans. The time to exhaustion after cycling was measured in subjects administered a sublingual tablet including tocotrienols versus placebo.

Compared to placebo treatment (92 minutes average), tocotrienol supplementation increased average cycling time to (133 minutes average), an increase of ~40% (FIG. 8).

Subjective measures of exhaustion were also more slowly reached during increments in exercise intensity, and the total calculated distance travelled was greater during the tocotrienol treatment (51 km) compared to placebo (32 km).

These results are in contrast to the only publication in exercising humans, which supplemented either placebo or a 50 mg daily oral dose of palm-based tocotrienols for 6 weeks in healthy young men, showing no increase in exercise time to exhaustion running on a treadmill, despite increases in plasma antioxidant status (Keong C C, Singh H J & Singh R. "Effects of palm vitamin E supplementation on exercise-induced oxidative stress and endurance performance in the heat". Journal of Sports Science and Medicine 5, 629-639).

Taken together, these 2 studies demonstrate that the sublingual route is important to the translation of the beneficial effects observed via oral administration in rats to effective outcomes in humans.

Example 4

Tocotrienol Supplementation Reduces Post Exercise Soreness and Delayed Onset Muscle Soreness (DOMS)

The subjects administered a sublingual formulation of tocotrienol described in Example 2 were assessed for post exercise soreness and DOMS.

DOMS was induced by slow eccentric contraction of the forearm in four subjects. Subjects were seated and rested their forearm and elbow on a table. They were required to lower a 10-12 kg (depending on ability to control the weight) dumbbell from an upright arm position to the table, taking 3 seconds. This was repeated for 3 sets of 12 repetitions, with a minute rest period between each set. Each subject performed this test at the end of a 3 week period of supplementation with sublingual tocotrienols (40 mg/d) or placebo sublingual tablets, in blinded and randomised order.

Figure 10:
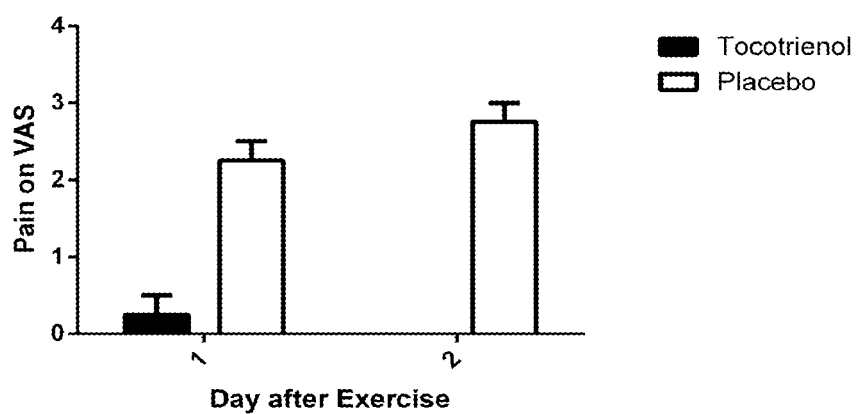
FIG. 10. Delayed onset muscle soreness on visual analogue scale 1 and 2 days after eccentric forearm contraction.

Pain ratings were assessed at 24 and 48 h after the exercise by two methods: a visual analogue scale of a 10 cm line where subjects were asked to rate their pain between 1-no pain and 10-extreme pain; additionally, subjects were asked to match their sensation to the descriptive phrases: no pain, dull ache, slight pain, more slight pain, moderate pain, severe pain, extreme pain. FIG. 10 shows the visual analogue rating for the 4 subjects where virtually no pain (0.25 at 24 h and 0 at 48 h) was experienced following tocotrienol supplementation, compared to ratings of slight pain to more slight pain following placebo supplementation (2.25 at 24 h and 48 h).

Further, subjects also volunteered pain ratings after exercise to exhaustion and following incidental exercise during tocotrienol and placebo treatment periods. Subjects rated their pain after exercise to exhaustion, being uniformly tired following on both supplements after exercise to exhaustion, but only experiencing the descriptors "muscle stiffness", "sore the next few days", "tired and unable to go again", "stiff with pain in adductors" when taking the placebo supplement.

During incidental exercise, subjects reported and little pain and more rapid recovery from exercise during tocotrienol supplementation compared to the placebo period.

Example 5

Increased Presence of Tocotrienols Concentrations in Blood Plasma Following Sublingual Delivery of Tocotrienols in Gel A gel formulation for sublingual delivery of tocotrienols was formulated as follows: Carboxymethyl cellulose 2% and polyethylene glycol (0.5%) in water to form a gel which is then admixed with DeltaGold (annatto-based 70% pure tocotrienol extract) to yield a 20 mg/ml tocotrienol gel.

A test was carried out in 2 subjects who administered 40 mg tocotrienols in 2 ml of gel sublingually. Blood samples were collected from a forearm venous catheter before administration and at 15, 60, and 180 minutes after administration.

Figure 9:
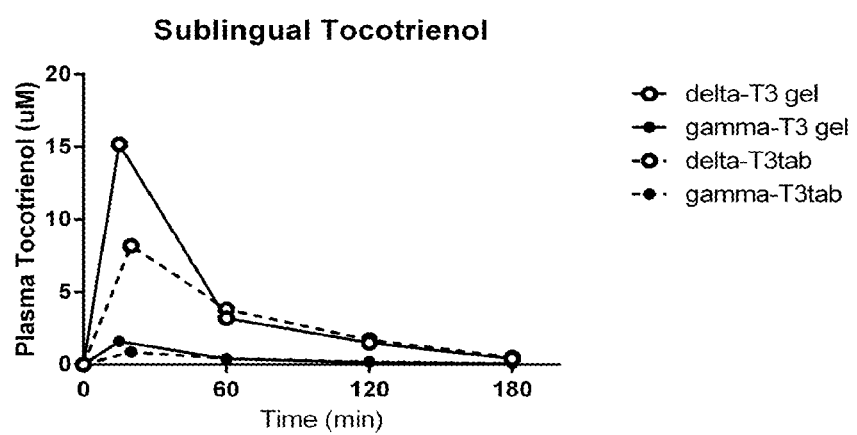
FIG. 9: Appearance of blood plasma concentrations using gel and tablet sublingual formulations of a 40 mg dose of tocotrienols. Delta tocotrienol (delta-T3) and gamma tocotrienol (gamma-T3) levels were measured in plasma at time points up to 180 minutes from administration of the gel or tablet (tab) formulation.

As shown in FIG. 9 tocotrienols appeared rapidly in plasma, with a level of 15 µM for the delta isomer at 15 minutes after administration, decreasing to 3.2 µM, 1.5 µM and 0.4 µM at 60 minutes, 120 minutes and 180 minutes after administration. The levels of delta and gamma tocotrienol in plasma retained their tablet composition ratio of 9:1, showing that both tocotrienols were equally well absorbed via the sublingual route. This is in contrast to the oral route, where there is a difference in plasma appearance of tocotrienols in the order: alpha tocotrienol>gamma tocotrienol>delta tocotrienol (Fairus S. et al, "Alpha-tocotrienol is the most abundant tocotrienol isomer circulated in plasma and lipoproteins after postprandial tocotrienol-rich vitamin E supplennentation", Nutrition Journal 2012, 11: 5).

Example 6

Increased Presence of Tocotrienols Concentrations in Blood Plasma Following Sublingual Delivery of Tocotrienols in Tablet Form A 220 mg sublingual tablet formulation was prepared containing a dose of 10 mg tocotrienol comprised of the actives: delta-tocotrienol 9 mg, gamma tocotrienol 1 mg; and the following excipients: dextrose, mannitol, marine gelatin, 1-leucine, 1-arginine, pre-gel starch, PEG-200, propylene glycol, talc, silica dioxide, magnesium stearate, carotenoids.

A test was carried out on 2 subjects who dissolved 4×10 mg tablets sublingually. Blood samples were collected from a forearm venous catheter before and after dissolution of the tablets (20 min); then at hourly intervals for 5 hours.

As shown in FIG. 9, delta and gamma tocotrienols appeared in plasma at high levels at the 20 minute point (8.2 µM for delta tocotrienol and 0.8 µM for gamma tocotrienol) and decreased over the next 3 hours (3.8 and 0.4 µM at 1 h; 1.7 and 0.19 µM and 0.02 at 2 h; 0.15 and 0.07 µM at 3 h).

While the plasma appearance of tocotrienols initially appears greater with the gel compared with the tablet, this is an artefact of the timing of sampling, as can be shown by the equivalent plasma levels achieved by both tablet and gel formulations at later time-points.

The tablets were effective in our measured parameters of reducing DOMS and increasing cycling exercise time during the incremental test to exhaustion.

An important difference between oral dosing and both of the sublingual formulations is the rapid appearance of tocotrienols in plasma, within minutes, compared to about 2 h for the oral route. Further, the CMax levels observed (albeit from this small number of participants) were greater for the 40 mg dose of sublingual tocotrienols than those achieved by the oral ingestion of higher doses (200 mg of individual tocotrienols; Hay Y K, et al http://www.tocotrienol.org/bioavailability-study.html).

Example 7

Tocotrienol Supplementation Reduces Inflammation

A 220 mg sublingual tablet formulation was prepared containing a dose of 10 mg tocotrienol comprised of the actives: delta-tocotrienol 9 mg, gamma tocotrienol 1 mg; and the following excipients: dextrose, mannitol, marine gelatin, 1-leucine, 1-arginine, pre-gel starch, PEG-200, propylene glycol, talc, silica dioxide, magnesium stearate, carotenoids.

One subject was administered two doses of 20 mg sublingual tocotrienol tablets in the morning and evening for a total of four weeks. Said subject reported a reduction in inflammation and relief from the pain of an oral abscess.

The same subject with benign prostate hypertrophy reported an increase in urine flow and volume during the tocotrienol supplementation, which gradually regressed to previous lower levels following the cessation of tocotrienol supplementation.

Persons skilled in the art will appreciate that variations and modifications will become apparent. All such variations and modification which become apparent to a person skilled in the art should be considered to fall within the spirit and scope of the invention as described.

The invention claimed is:

1. A pharmaceutical composition formulated for transmucosal delivery comprising at least one tocotrienol, together with one or more pharmaceutically acceptable excipients, wherein the at least one tocotrienol comprises delta-tocotrienol.

2. The pharmaceutical composition according to claim 1, wherein the transmucosal delivery is sublingual and/or buccal delivery.

3. The pharmaceutical composition according to claim 1, wherein the composition comprises at least one tocotrienol and at least one tocopherol, wherein the tocopherol component is lower than the tocotrienol component.

4. The pharmaceutical composition according to claim 3, wherein the composition comprises less than about 10% tocopherol.

5. The pharmaceutical composition according to claim 1, wherein the composition contains no tocopherol.

6. The pharmaceutical composition according to claim 1, wherein the at least one tocotrienol further comprises alpha-tocotrienol, beta-tocotrienol, gamma tocotrienol, or a combination thereof.

7. The pharmaceutical composition according to claim 1, wherein the at least one tocotrienol further comprises gamma tocotrienol.

8. The pharmaceutical composition according to claim 1, wherein
- the one or more pharmaceutically acceptable excipients is polyethylene glycol,
- the composition is formulated for sublingual or buccal delivery in the transmucosal environment of an animal.

9. The pharmaceutical composition according to claim 1, wherein the composition is in the form of a tablet, film, wafer, gum, powder, spray, solution or gel.

10. The pharmaceutical composition according to claim 1, wherein at least one of the one or more pharmaceutically acceptable excipients is marine gelatin.

11. The pharmaceutical composition according to claim 1, wherein the one or more pharmaceutically acceptable excipients are selected from among the group consisting of: dextrose, mannitol, marine gelatin, L-leucine, L-arginine, pre-gel starch, PEG-200, propylene glycol, talc, silica dioxide, magnesium stearate and carotenoids.

* * * * *